US006359129B1

(12) United States Patent
Hanson et al.

(10) Patent No.: US 6,359,129 B1
(45) Date of Patent: Mar. 19, 2002

(54) AMINO ACID-DERIVED, 7-MEMBERED CYCLIC SULFAMIDES AND METHODS OF SYNTHESIZING THE SAME

(75) Inventors: Paul R. Hanson; Joseph M. Dougherty; Donald A. Probst, all of Lawrence, KS (US)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 09/639,023

(22) Filed: Aug. 15, 2000

(51) Int. Cl.⁷ ............................................. C07D 285/36
(52) U.S. Cl. ..................................................... 540/545
(58) Field of Search ........................................ 540/545

(56) References Cited

U.S. PATENT DOCUMENTS

| | | | |
|---|---|---|---|
| 3,329,687 A | 7/1967 | Houlihan | 260/327 |
| 5,312,940 A | 5/1994 | Grubbs et al. | 556/136 |
| 5,342,909 A | 8/1994 | Grubbs et al. | 526/171 |
| 5,506,355 A | 4/1996 | Jadhav et al. | 540/545 |
| 5,610,294 A | 3/1997 | Lam et al. | 540/492 |
| 5,710,298 A | 1/1998 | Grubbs et al. | 556/22 |
| 5,750,815 A | 5/1998 | Grubbs et al. | 585/511 |
| 5,917,071 A | 6/1999 | Grubbs et al. | 556/21 |
| 6,048,993 A | 4/2000 | Grubbs et al. | 556/21 |

FOREIGN PATENT DOCUMENTS

| | | |
|---|---|---|
| WO | 9419329 | 9/1994 |
| WO | 9937643 | 7/1999 |

OTHER PUBLICATIONS

Zhu, S. et al., "Chiral Mo–Binol Complexes: Activity, Synthesis, and Structure, Efficient Enantioselective Six–Membered Ring Synthesis Through Catalytic Metathesis" *J. Am. Chem. Soc.*, 1999, 121, 8251–8259.
Kingsbury, J. et al., "A Recyclable Ru–Based Metathesis Catalyst", *J. Am. Chem. Soc.*, 1999, 121, 791–799.
Scholl, M. et al., Synthesis and Activity of a New Generation of Ruthenium–Based Olefin Metathesis Catalysts Coordinated With 1,3–Dimesityl–4,5–dihydroimidazol–2–ylidene Ligands§, *Org. Lett.*, vol. 1, No. 6, 1999, 953–956.
Totland, K. et al., "Ring Opening Metathesis Polymerization With Binaphtholate or Biphenolate Complexes of Molybdenum", *Macromolecules*, 1996, 29, 6114–6125.
Alexander, J. et al., "Catalytic Enantioselective Ring–Closing Metathesis by a Chiral Biphen–Mo Complex", *J. Am. Chem. Soc.*, 1998, 120, 4041–4042.
Bäckbro, K., "Unexpected Binding Mode of Cyclic Sulfamide HIV–1 Protease Inhibitor", *J. Med. Chem.*, 1997, 40, 898–902.
Hultén, J. et al., "Inhibitors of the $c_2$–Symmetric HIV–1 Protease: Nonsymmetric Binding of a Symmetric Cyclic Sulfamide With Ketoxime Groups in the P2/P2' Side Chains", . *J. Med. Chem.*, 1999, 42, 4054–4061.

*Primary Examiner*—Bruck Kifle
(74) *Attorney, Agent, or Firm*—Hovey Williams LLP

(57) ABSTRACT

New sulfamide compounds and methods of forming those compounds are provided. The inventive methods comprise subjecting a template opened-ring sulfamide compound to a ring-closing metathesis reaction in the presence of a Grubbs catalyst to yield a heterocyclic sulfamide. Advantageously, the template structures can be provided with a wide array of functional groups (e.g., substituted and unsubstituted amino acid side chains, peptides) chosen to provide particular properties to the compound. The preferred heterocyclic sulfamides are represented by a formula selected from the group consisting of

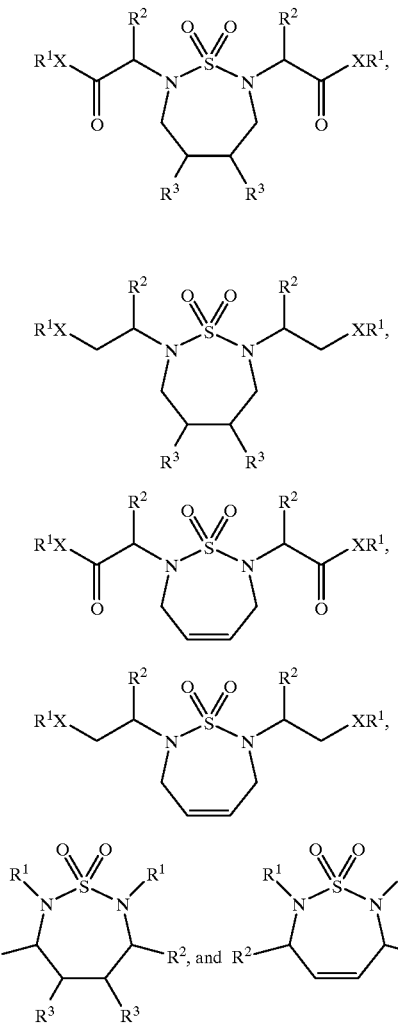

13 Claims, No Drawings

AMINO ACID-DERIVED, 7-MEMBERED CYCLIC SULFAMIDES AND METHODS OF SYNTHESIZING THE SAME

BACKGROUND OF THE INVENTION

1. Field of the Invention

The present invention is directed towards new sulfamide compounds and methods of forming those compounds via ring-closing metathesis reactions carried out in the presence of a ring-closing catalyst such as an olefin metathesis catalyst (e.g., a Grubbs catalyst). The compounds have a number of uses including as inhibitors of enzymes such as HIV proteases.

2. Description of the Prior Art

Small peptides are excellent starting points for drug design because they have the potential to overcome the pharmacokinetic shortcomings of larger peptides, yet retain the desirable quality of molecular recognition. A number of dipeptides are currently being developed as novel pharmaceutical agents (see e.g., Blackburn et al., *Bioorg. Med. Chem. Lett.*, 7:823–26 (1997); Schullek et al., *Anal. Biochem.*, 246:20–29 (1997), each incorporated by reference herein). Unfortunately, even small peptides suffer from proteolytic instability which limits their use as drug candidates.

Peptide mimics have been developed that utilize the urea moiety as a non-hydrolyzable linker and/or a hydrogen bond acceptor. Further modifications to cyclic ureas have led to the generation of a new sub-class of biologically active compounds. A number of cyclic HIV protease inhibitors have been developed that incorporate ureas, sulfamides, and other urea surrogates as the central linchpin. In these cases, it has been shown that the H-bonding urea moieties may serve to replace the water molecule exclusive to the active site of HIV protease. Ring-closing metathesis (RCM) reactions have become a highly effective strategy for the construction of a number of important heterocyclic compounds (see e.g., Fu et al., *J. Am. Chem. Soc.*, 115:9856 (1993), incorporated by reference herein) and constrained peptides (see e.g., Miller et al., *J. Am. Chem. Soc.*, 117:5855–5856 (1995); Miller et al., *J. Am. Chem. Soc.*, 118:9606–9614 (1996); Blackwell et al., *Angew. Chem., Int. Ed.*, 37:3281–3284 (1998), each incorporated by reference herein).

Sulfamides are unique functional groups that have been exploited in the development of a number of novel pharmaceutical agents and synthetic ligands. Their ability to serve as urea surrogates have made them ideal functional groups for the development of novel peptidomimetics, while their chelating ability has made them ideal for the development of novel ligands for asymmetric catalytic reactions. This diverse set of properties has made them important targets in the development of new chemical entities.

Since its discovery as the causative agent of AIDS, considerable effort has been placed on understanding the biomolecular replicative process of the human immunodeficiency virus (HIV), with primary focus being placed on the inhibition of a key virally encoded protease enzyme of the pol gene. Many synthetic approaches to the inhibition of HIV protease are based on the synthesis of peptidomimetics which replace a key scissile amide bond by a non-hydrolyzable transition state isostere. This strategy has been employed to synthesize a number of novel nonpeptidal HIV protease inhibitors. Among the more effective peptidomimetics, the synthesis of cyclic ureas (see e.g., Lucca et al., *Drugs of the Future*, 23:987 (1998)), cyclic sulfamides (see e.g., Jadhav et al., *Tetrahedron Lett.*, 36:6383 (1995)), hydroxyethylene/hydroxyethylamine isosteres (see e.g., Thomas et al., *Biorg. Med. Chem. Lett.*, 4:2759 (1994)) have been reported.

SUMMARY OF THE INVENTION

The present invention is broadly concerned with new sulfamide compounds and methods of forming such compounds. In more detail, the compounds are represented by a formula selected from the group consisting of

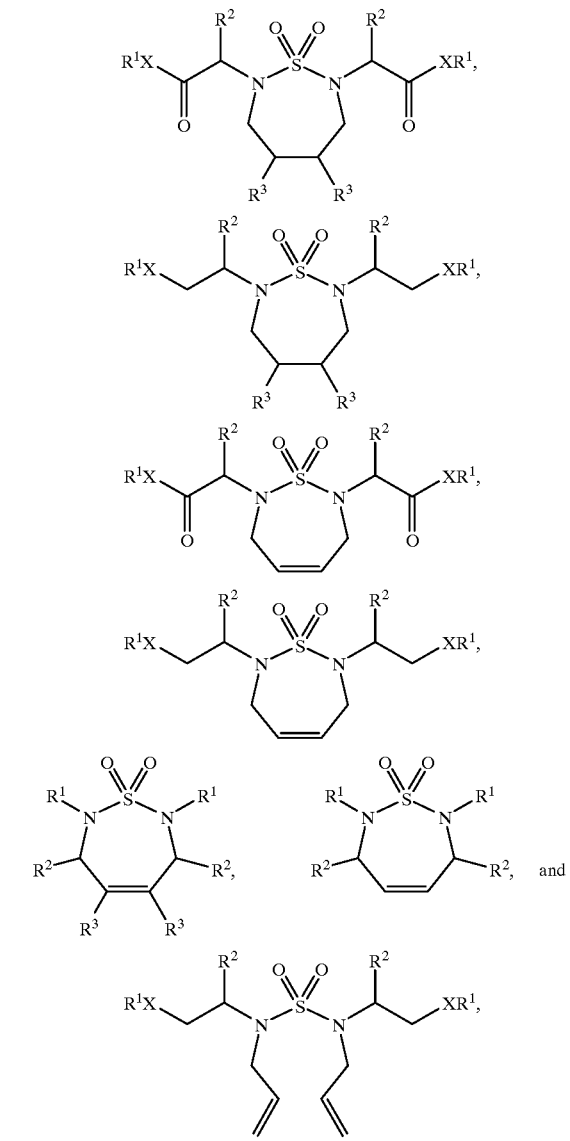

wherein:
each X is individually selected from the group consisting of oxygen, —NH, and —NOR$^1$,
each R$^1$ is individually selected from the group consisting of hydrogen, branched and unbranched alkyl groups (preferably $C_1$–$C_{18}$, more preferably $C_1$–$C_8$), branched and unbranched alkenyl groups (preferably $C_2$–$C_{18}$, more preferably $C_2$–$C_8$), branched and unbranched alkynyl groups (preferably $C_2$–$C_{18}$, more preferably $C_2$–$C_8$), allyl groups, acyl groups (preferably $C_2$–$C_{18}$, more preferably $C_1$–$C_8$), aryl groups (preferably $C_6$–$C_{12}$), 2–15 mer peptides, and benzyl groups;

each $R^2$ is individually selected from the group consisting of hydrogen, substituted and unsubstituted amino acid side chains, and 2–15 mer peptides; and each $R^3$ is individually selected from the group consisting of hydrogen, —OH, and —$NHR^1$, with $R^1$ being as defined above.

Preferably at least one $R^2$ group comprises an amino acid side chain selected from the group consisting of

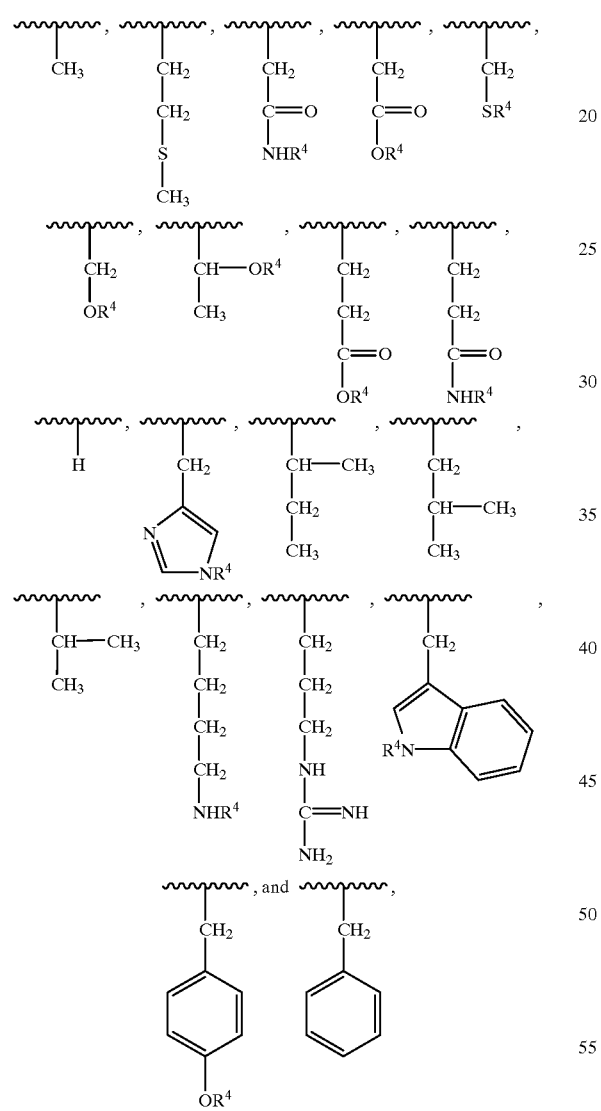

wherein each $R^4$ is individually selected from the group consisting of hydrogen, branched and unbranched alkyl groups (preferably $C_1$–$C_{18}$, more preferably $C_1$–$C_8$), branched and unbranched alkenyl groups (preferably $C_2$–$C_{18}$, more preferably $C_2$–$C_8$), branched and unbranched alkynyl groups (preferably $C_2$–$C_{18}$, more preferably $C_2$–$C_8$), allyl groups, aryl groups (preferably $C_6$–$C_{12}$), acyl groups (preferably $C_2$–$C_{18}$, more preferably $C_2$–$C_8$), and benzyl groups.

Particularly preferred compounds according to the invention are those selected from the group consisting of

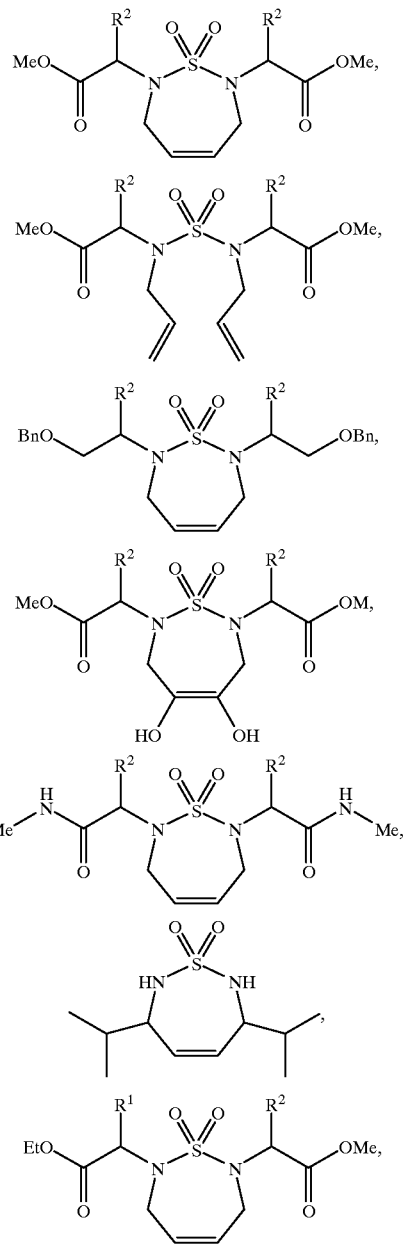

wherein each $R^2$ is individually selected from the group consisting of —$CH_3$, —$CH(CH_3)_2$, —$CH_2CH(CH_3)_2$, and —$CH_2Ph$.

The inventive compounds are formed by reacting a template sulfamide compound which comprises an opened-ring structure (i.e., a partially-formed ring comprising at least half, but not all of the sides necessary to form a cyclic compound) with a ring-closing catalyst to yield the closed-ring phosphonamide compound. Preferred ring-closing catalysts are olefin metathesis catalysts such as Grubbs catalysts (see e.g., U.S. Pat. Nos. 6,048,993, 5,917,071, 5,750,815, 5,710,298, 5,342,909, and 5,312,940, each incorporated by reference herein) as well as those disclosed by the following references, each also incorporated by reference herein: Matthias, *Org. Ltrs.,* 1(6):953–56 (1999); Schrock, Macromolecules, 29(19):6114–25 (1996); Zhu et al., J. Amer. Chem. Soc., 121(36):8251–59 (1999); Alexander et al., J. Amer. Chem. Soc., 120(16):4041–42 (1998); and Kingsbury et al., J. Amer. Chem. Soc., 121(4):791–99 (1999).

Particularly preferred Grubbs catalysts are those selected from the group consisting of

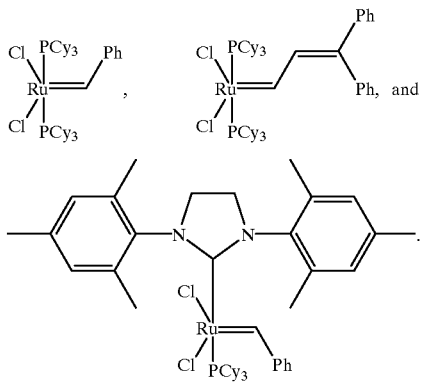

Preferred template structures comprise an allylated sulfamide, with particularly preferred template structures being those selected from the group consisting of

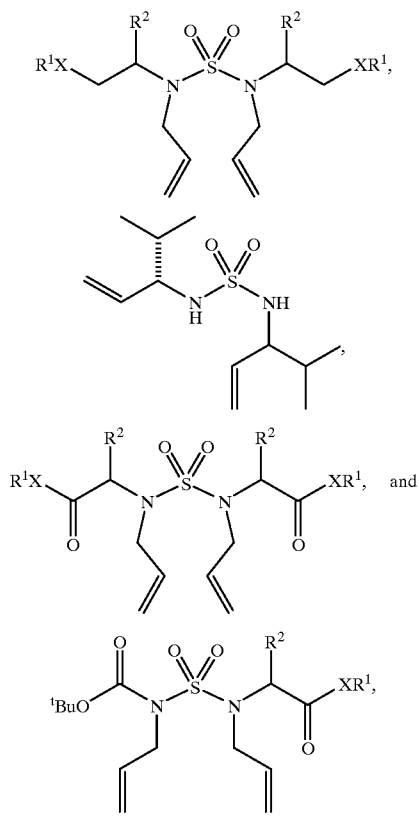

wherein:
each X is individually selected from the group consisting of oxygen, —NH, and —NOR$^1$;
each R$^1$ is individually selected from the group consisting of hydrogen, branched and unbranched alkyl groups (preferably C$_1$–C$_{18}$, more preferably C$_1$–C$_8$), branched and unbranched alkenyl groups (preferably C$_2$–C$_{18}$, more preferably C$_2$–C$_8$), branched and unbranched alkynyl groups (preferably C$_2$–C$_{18}$, more preferably C$_2$–C$_8$), allyl groups, acyl groups (preferably C$_6$–C$_{18}$, more preferably C$_1$–C$_8$) aryl groups (preferably C$_6$–C$_{12}$), 2–15 mer peptides, and benzyl groups; and
each R$^2$ is individually selected from the group consisting of hydrogen, substituted and unsubstituted amino acid side chains, and 2–15 mer peptides.

Preferably the reacting step is carried out at a temperature of from about 15–80° C., and more preferably from about 30–55° C. Furthermore, the reacting step should be carried out in a solvent system comprising a solvent selected from the group consisting of toluene, benzene, chlorobenzene, dichlorobenzene, methylene chloride, dimethoxyethane, methanol, water, and mixtures thereof. Preparing the ringed sulfamide compounds according to the inventive methods should result in a yield of those compounds of at least about 70%, and preferably at least about 90%, wherein the theoretical yield is taken as 100%.

It will be appreciated that the inventive methods allow for the synthesis of a wide array of both symmetric and unsymmetric cyclic sulfamide compounds. Furthermore, the inventive methods allow for preparation of, or selection of, templates having particular functional groups bonded thereto which are then readily formed into the desired sulfamide in a controlled and repeatable manner. Because the method can be adapted to form sulfamide compounds comprising one or more amino acid side chains or peptides bonded thereto, the inventive compounds can be used to inhibit HIV proteases, carbonic anhydrase, renin, and other enzymes. The inventive compounds may also be used as retroviral inhibitors, anti-inflammatory agents, bioadhesion inhibitors, and herbicides.

DETAILED DESCRIPTION OF THE PREFERRED EMBODIMENTS

EXAMPLES

The following examples set forth preferred methods in accordance with the invention. It is to be understood, however, that these examples are provided by way of illustration and nothing therein should be taken as a limitation upon the overall scope of the invention.

A number of abbreviations are used herein. These abbreviations and the term or terms that they represent are set forth in Table A.

TABLE A

| Abbreviation | Term(s) |
| --- | --- |
| hex | hexane |
| Bn | benzyl |
| Ph | phenyl |
| Me | methyl |
| Et | ethyl |
| Boc | butoxy carbonyl |
| EtOAc | ethyl acetate |
| Et$_3$N | triethyl amine |
| $^t$BuO | tert-butoxy |

Grubbs Catalysts were used in some of the following Examples. These catalysts are referred to as follows:

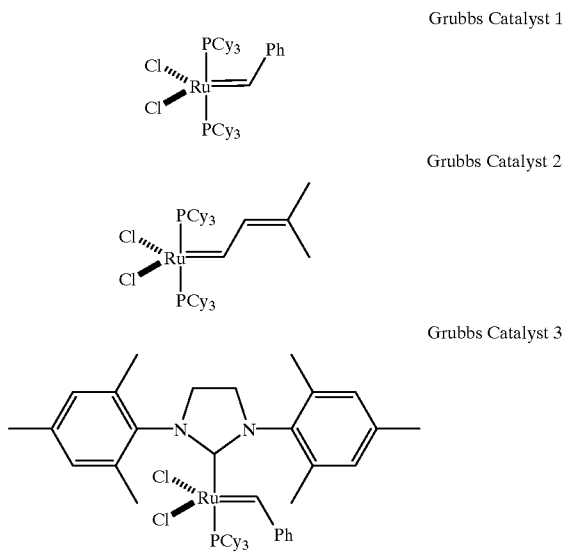

Grubbs Catalyst 1

Grubbs Catalyst 2

Grubbs Catalyst 3

Example 1

The overall reaction scheme followed in Examples 1A–1C below is set forth in Scheme A.

Example 1A

In the following parts I–IV of this example, compounds 7a–7d were used to prepare compounds 8a–8d, respectively. Scheme B depicts these compounds and the reaction in this portion. In this and the following procedure descriptions, the number/letter abbreviation depicted in the particular reaction scheme follows the chemical name of the particular compound (e.g., "(8b)" follows "N,N'-Sulfonyl bis-L-valine dimethyl ester").

Scheme B

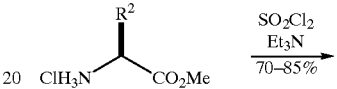

7a: $R^2 = CH_3$
7b: $R^2 = CH(CH_3)_2$
7c: $R^2 = CH_2CH(CH_3)_2$
7d: $R^2 = CH_2Ph$

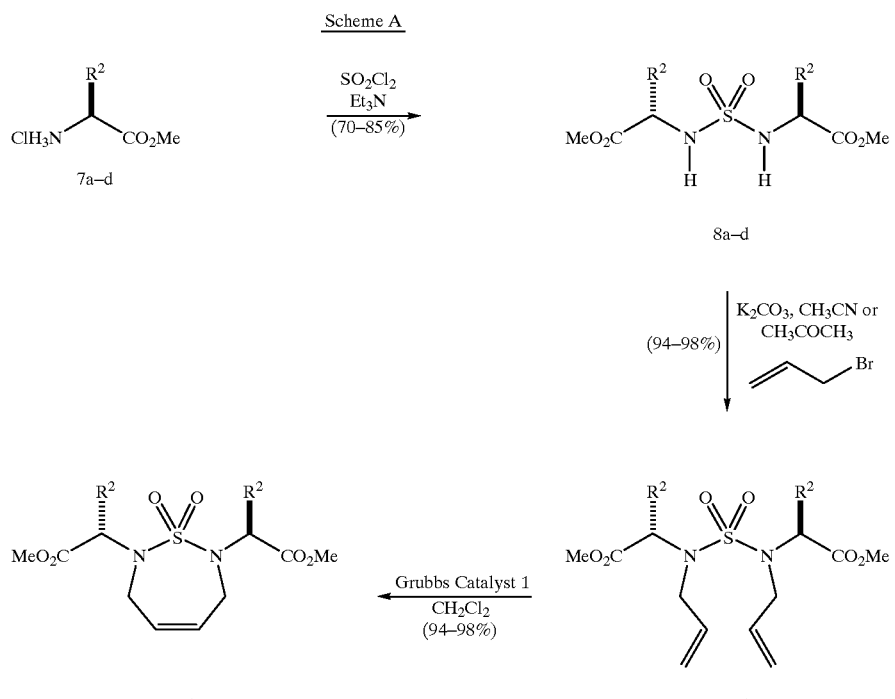

a: $R^2 = CH_3$
b: $R^2 = CH(CH_3)_2$
c: $R^2 = CH_2CH(CH_3)_2$
d: $R^2 = CH_2Ph$

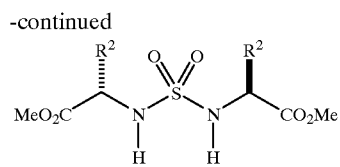

8a: R² = CH₃
8b: R² = CH(CH₃)₂
8c: R² = CH₂CH(CH₃)₂
8d: R² = CH₂Ph

I. Preparation of N,N'-Sulfonyl bis-L-valine Dimethyl Ester (8b)

H-Val-OMe.HCl (7b) (2.61 g, 15.56 mmol) and CH₂Cl₂ (85 mL) were added sequentially to a 250 mL round-bottom flask. The solution was cooled to 0° C., Et₃N (4.50 g, 44.5 mmol) added slowly, and the resulting solution was stirred for 15 min. SO₂Cl₂ (595 µL, 1.00 g, 7.41 mmol) was added slowly over 45 minutes, and the resulting yellow solution was then warmed to room temperature over 3 hours. The solvent was concentrated to 15 mL under reduced pressure, EtOAc (225 mL) was added, and the solution was washed twice with 10% NaHSO₄, aqueous NaHCO₃, brine, and dried MgSO₄). The solution was filtered and concentrated under reduced pressure to leave a crude oil. Flash chromatography (SiO₂, Hexanes/EtOAc) afforded 1.98 g (82.6%) of sulfamide (8b) as a white solid. mp=76–77° C.; TLC $R_f$=0.58 (2:1 Hexanes/EtOAc); $[\alpha]^{25}_D$=+14.2(c=1.02, CHCl₃); ¹H NMR (CDCl₃, 400 MHZ) δ5.01 (d, J=9.6 Hz, 2H), 3.88 (dd, J=9.6, 4.4 Hz, 2H), 3.77 (s, 6H), 2.18–2.10 (m, 2H), 1.00 (d, J=6.9 Hz, 6H), 0.88 (d, J=6.9 Hz, 6H); ¹³C NMR (CDCl₃, 100 MHZ) δ172.9,61.1, 52.4, 31.5, 18.8, 17.4; FTIR (neat) 3317, 3266, 1737, 1466, 1355, 1327, 1137 cm⁻¹; HRMS (M+H)⁺ calculated for C₁₂H₂₅N₂O₆S 325.1437, found 325.1432.

II. Preparation of N,N'-Sulfonyl bis-L-alanine Dimethyl Ester (8a)

In a procedure similar to the preparation of sulfamide (8b), H-Ala-OMe.HCl (2.18 g, 15.56 mmol) was subjected to sulfamide formation conditions (SO₂Cl₂, Et₃N, CH₂Cl₂ 0° C., room temperature, 2 hours). Flash chromatography (SiO₂, Hexanes/EtOAc) yielded 617 mg (31%) of sulfamide (8a) as a white solid. mp=91–92° C.; TLC $R_f$=0.40 in (2:1 Hexanes/EtOAc); $[\alpha]^{25}_D$=−75.8 (c=1.003, CHCl₃); ¹H NMR (CDCl₃, 400 MHZ) δ5.24 (d, J=8.0 Hz, 2H), 4.09 (dq, J=7.3.7.3 Hz, 2H), 3.75 (s, 6H), 1.43 (d, J=7.2 Hz, 6H); ¹³C NMR (CDCl₃, 100 MHZ) δ173.7,52.7,51.8,19.2; FTIR (neat) 3273, 1734, 1457, 1378, 1353, 1137 cm⁻¹; HRMS (M+H)⁺ calculated for C₈H₁₇N₂O₆S 269.0807, found 269.0791.

III. Preparation of N,N'-Sulfonyl bis-L-leucine Dimethyl Ester (8c) and N,N'-Sulfonyl bis-L-phenylalanine Dimethyl Ester (8d)

N,N'-Sulfonyl bis-L-leucine dimethyl ester (8c) and N,N'-Sulfonyl bis-L-phenylalanine dimethyl ester (8d) were prepared according to the procedure described by Sowada, *J. Prakt. Chem.* 20:310 (1963) and McDermott et al., *Org. Prep. Proc. Int.* 16:49–77 (1984), each being incorporated by reference herein.

IV. Preparation of N,N'-Sulfonyl bis[(R)-1-phenylethylamine] (8e)

In a procedure similar to the preparation of sulfamide (8b), (R)-phenethylamine (471 mg, 501 µL, 3.84mmol) was subjected to sulfamide formation conditions (SO₂Cl₂, Et₃N, CH₂Cl₂ 0° C.-RT, 8 h). Flash chromatography (SiO₂, Hexanes/EtOAc) yielded 356 mg (63%) of sulfamide (8e) as a white solid. mp=96–97° C.; TLC $R_f$=0.37 (3:1 Hexanes/EtOAc); $[\alpha]^{25}_D$=−31.2 (c=1.02, CHCl₃); ¹H NMR (CDCl₃, 400 MHZ) δ7.27–7.21 (m, 6H), 7.17–7.14 (m, 4H), 4.74 (s, 2H), 4.43 (dq, J=12.2. 6.2 Hz, 2H), 1.46 (d, J=6.8Hz, 6H); ¹³C NMR (CDCl₃, 100 MHZ) δ142.7, 128.6, 127.5, 126.1, 53.7, 23.6; FTIR(neat) 3312,3032,2992,2944,1603,1493, 1454,1381,1320,1149,751,701 cm⁻¹; HRMS (M+H)⁺ calculated for C₁₆H₂₁N₂O₂S 305.1324, found 305.1322.

In Parts I–IV of this procedure, methylene chloride was the solvent utilized. However, acetonitrile, chloroform, toluene, benzene, chlorobenzene, dichlorobenzene, tetrahydrofuran (THF), diethyl ether, acetone, dimethoxyethane (DME), and mixtures thereof are also suitable solvents. Furthermore, while Et₃N was used as the base, other bases which could be used included pyridine, NaHCO₃, Na₂CO₃, K₂CO₃, NaH, KH, any tertiary amine, and mixtures thereof. Finally, while the procedure was carried out at temperatures of 0–20° C., temperatures of anywhere from about −20–20° C. would also be suitable.

Example 1B

In the following parts I–V of this example, compounds 8a–8e were used to prepare compounds 9a–9e, respectively. Scheme C depicts these compounds and the reactions.

Scheme C

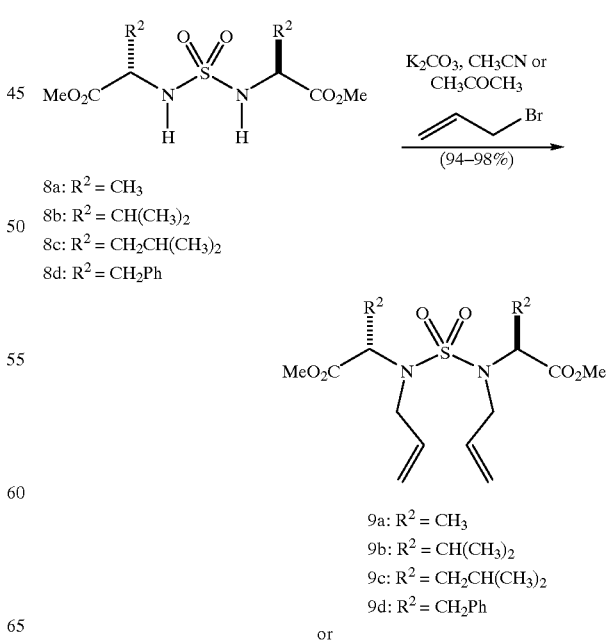

8a: R² = CH₃
8b: R² = CH(CH₃)₂
8c: R² = CH₂CH(CH₃)₂
8d: R² = CH₂Ph

9a: R² = CH₃
9b: R² = CH(CH₃)₂
9c: R² = CH₂CH(CH₃)₂
9d: R² = CH₂Ph or

-continued

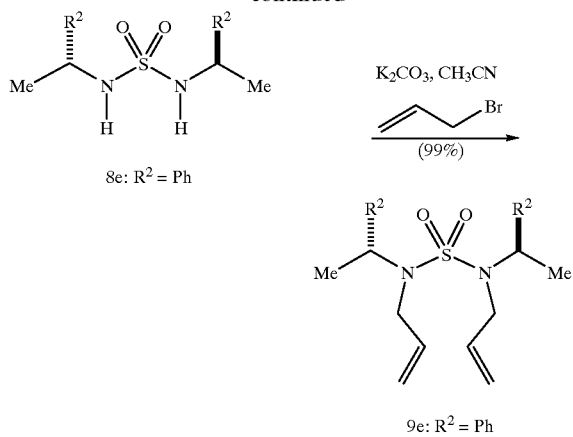

8e: R² = Ph

K₂CO₃, CH₃CN
Br
(99%)

9e: R² = Ph

I. Preparation of N,N'-Bis(2-propenyl)-N,N'-sulfonyl bis-L-valine Dimethyl Ester (9b)

K₂CO₃(1.06 g, 7.70 mmol) and allyl bromide were added to a stirring solution of sulfamide (8b) (500 mg, 1.54 mmol) in CH₃CN (35 mL) in a 100 mL round-bottom flask (1.12 g, 9.24 mmol). The flask was fitted with a condenser, and the mixture was heated to 70° C. for 14 hours. The resulting yellow orange mixture was filtered by suction, and the solvent was removed under reduced pressure to give a yellow oil. Flash Chromatography (SiO₂, 10:1 Hexanes/EtOAc) afforded 619 mg (98.7%) of sulfamide (9b) as a clear oil. TLC $R_f$=0.31 (10:1 Hexanes/EtOAc); $[\alpha]^{25}_D$=−89.3 (c=1.00, CHCl₃); ¹H NMR (CDCl₃, 400 MHZ) 5.92 (dddd, J=15.9, 10.2, 7.5, 5.7 Hz, 2H), 5.14 (dd, J=16, 1.3 Hz, 2H), 5.05 (dd, J=10.2, 1.2 Hz, 2H), 3.99–3.90 (m, 6H), 3.68 (s, 6H), 2.16–2.08 (m, 2H), 0.97 (d, J=6.7 Hz, 6H), 0.86 (d, J=6.6, 6H); ¹³C NMR (CDCl₃, 100MHZ) 171.6, 135.2, 117.3, 66.3, 51.5, 47.7,28.4, 19.6, 19.5; FTIR (neat) 3080, 1745, 1640, 1436, 1351, 1137 cm⁻¹; HRMS (M+H)⁺ calculated for C₁₈H₃₃N₂O₆S 405.2059, found 405.2031.

II. Preparation of N'-Bis(2-propenyl)-N,N'-sulfonyl bis-L-alanine Dimethyl Ester (9a)

In a procedure similar to that used for the preparation of the allylated sulfamide (9b), sulfamide (8a) (500 mg, 1.86 mmol) was subjected to standard allylation procedures (K₂CO₃, allyl bromide, CH₃CN 70° C., 18 hours). Flash chromatography (SiO₂, Hexanes/EtOAc) yielded 596 mg (92%) of sulfamide (9a) as a yellow oil. TLC $R_f$=0.53 (3:1 Hexanes/EtOAc);$[\alpha]^{25}_D$=−20.3 (c=1.004, CHCl₃); ¹H NMR (CDCl₃, 400 MHZ) 5.87 (dddd, J=16.8, 10.5, 6.5, 6.3 Hz, 2H), 5.24 (dd, J=15.9, 1.4 Hz, 2H), 5.16(dd, J=10.2, 1.2 Hz, 2H), 4.37 (q, J=7.2 Hz,2H),3.98 (dddd, J=16.1, 6.1, 1.1, 1.1 Hz, 2H), 3.77 (dddd, J=16.1, 6.7, 1.1, 1.1 Hz, 2H)3.72(s, 6H), 1.47 (d, J=4.2 Hz, 6H); ¹³C NMR (CDCl₃, 100 MHZ) 172.0, 134.4, 118.0, 55.0, 52.0, 48.8, 15.3; FTIR (neat) 1743, 1645, 1333, 1226 cm⁻¹; HRMS (M+H)⁺ calculated for C₁₄H₂₅N₂O₆S 349.1433, found 399.1436.

III. Preparation of N,N'-Bis(2-propenyl)-N,N'-sulfonyl bis-L-leucine Dimethyl Ester (9c)

In a procedure similar to that used for the preparation of the allylated sulfamide (9b), sulfamide (8c) (2.08 g, 5.88 mmol) was subjected to standard allylation procedures (K₂CO₃, allyl bromide, refluxing acetone, 48 hours). Flash chromatography (SiO₂, Hexanes/EtOAc) yielded 2.22 g (87%) of sulfamide (9c) as a yellow oil. TLC $R_f$=0.64 (2:1 Hexanes/EtOAc); $[\alpha]^{25}_D$=−42.5 (c=0.51, CDCl₃); ¹H NMR (CDCl₃, 400 MHZ) 5.90 (dddd, J=17.2, 10.2, 6.8, 6.1 Hz, 2H), 5.20 (dd, J=17.2, 1.3 Hz, 2H), 5.13 (dd, J=10.2, 1.1 Hz, 2H) 4.38 (dd, J=8.2, 6.0 Hz, 2H), 3.96 (dd, J=16.2, 6.0 Hz, 2H), 3.86 (dd, J=16.2, 7.0 Hz, 2H) 3.72 (s, 6H), 1.81–1.66 (m, 6H), 0.96 (d, J=6.1 Hz, 6H), 0.91 (d, J=6.2 Hz, 6H) ¹³C NMR (CDCl₃, 100 MHZ) 172.4, 134.9, 117.8, 58.1, 52.0, 48.7, 38.7, 24.4, 22.4, 21.8; FTIR (neat) 3074, 1746, 1641, 1344, 1169 cm⁻¹; HRMS (M+H)⁺ calculated for C₂₀H₃₇N₂O₆S 433.2372, found 433.2397.

IV. Preparation of N,N'-Bis(2-propenyl)-N,N'-sulfonyl bis-L-phenyl Alanine Dimethyl Ester (9d)

In a procedure similar to that used for the preparation of allylated sulfamide (9b), sulfamide (8d) (500 mg, 1.19 mmol) was subjected standard allylation procedures (K₂CO₃, allyl bromide, CH₃CN 70° C., 10 hours). Flash chromatography (SiO₂, Hexanes/EtOAc) yielded 560 mg (95%) of sulfamide (9d) as a yellow oil. TLC $R_f$=0.15 (10:1 Hexanes/EtOAc); $[\alpha]^{25}_D$=−47.9 (c=1.012, CHCl₃); ¹H NMR (CDCl₃, 400 MHZ) 7.28–7.25 (m, 8H), 7.22–7.19 (m, 2H), 5.77 (dddd, J=16.8, 10.5, 6.5, 6.5 Hz, 2H), 5.17–5.13 (nfom, 4H), 4.51 (dd, J=7.3, 7.3 Hz, 2H), 3.71 (dd, J=15.9, 6.3 Hz 2H), 3.66 (s, 6H), 3.58 (dd, J=15.9, 6.9 Hz, 2H), 3.40 (dd, J=14.1, 7.6 Hz, 2H), 3.07 (dd, J=14.1, 7.1 Hz, 2H); ¹³C NMR (CDCl₃, 100 MHz) 171.0, 137.3, 134.0, 129.2, 128.3, 126.7, 118.6, 61.0, 52.0, 48.8, 35.9; FTIR(neat) 3064, 3029, 1742, 1653, 1559, 1497, 1456, 1436, 1339, 1149, 743, 700 cm⁻¹; HRMS (M+H)⁺ calculated for C₂₆H₃₃N₂O₆S 501.2059, found 501.2043.

V. Preparation of N,N'-Bis(2-propenyl)-N,N'-sulfonyl bis [(R)-1-phenyl-ethylamine] (9e)

In a procedure similar to that used for the preparation of allylated sulfamide (9b), sulfamide (8e) (250 mg, 0.821 mmol) was subjected standard allylation procedures (K₂CO₃, allyl bromide, CH₃CN 70° C., 24 hours). Flash chromatography (SiO₂, Hexanes/EtOAc) yielded 313 mg (99%) of sulfamide (9e) as a clear oil. TLC $R_f$=0.59 (10:1 Hexanes/EtOAc); $[\alpha]^{25}_D$=+77.5 (c=1.00, CHCl₃); ¹H NMR (CDCl₃, 400 MHz) 7.46 (d, J=7.4 Hz, 4H), 7.39–7.35 (m, 4H), 7.32–7.30 (m, 2H), 5.79 (dddd, J=15.7, 9.7, 7.1, 5.8 Hz, 2H), 5.19 (q, J=7.1 Hz, 2H), 5.03 (dd, J=6.1, 1.3 Hz, 2H), 5.01–4.99 (m, 2H), 3.77 (dd with small allylic coupling, J=16.3, 5.8 Hz, 2H), 3.55 (dd, J=16.3, 7.2 Hz, 2H), 1.67 (d, J=7.1 Hz, 6H); ¹³C NMR (CDCl₃, 100 MHz) 140.1, 135.9, 128.2, 127.9, 127.5, 116.9, 56.5, 47.3, 17.9; FTIR(neat) 3064, 3030, 2980, 2937, 1640, 1603, 1496, 1452, 1378, 1323, 1161, 784, 699 cm⁻¹; HRMS (M+H)⁺ calculated for C₂₂H₂₉N₂O₂S 385.1950, found 385.1958.

In Parts I–V of this procedure, acetone was the solvent utilized. However, acetonitrile, chloroform, toluene, benzene, chlorobenzene, dichlorobenzene, THF, diethyl ether, methylene chloride, DME, and mixtures thereof are also suitable solvents. Furthermore, while K₂CO₃ was used as the base, other bases which could be used included pyridine, NaHCO₃, Na₂CO₃, NaH, KH, and mixtures thereof. The allylating agent utilized was allyl bromide, but the following would work as well: allyl iodide; allyl bromide, NaI; allyl bromide, KI; and allyl bromide, Bu₄NI. Finally, while the procedure was carried out at a temperature of 56° C. or 82° C., temperatures of anywhere from about 40–100° C. would also be suitable.

Example 1C

In the following parts I–V of this example, compounds 9a–9e were used to prepare compounds 4a–4e, respectively. Scheme D depicts these compounds and the reactions.

Scheme D

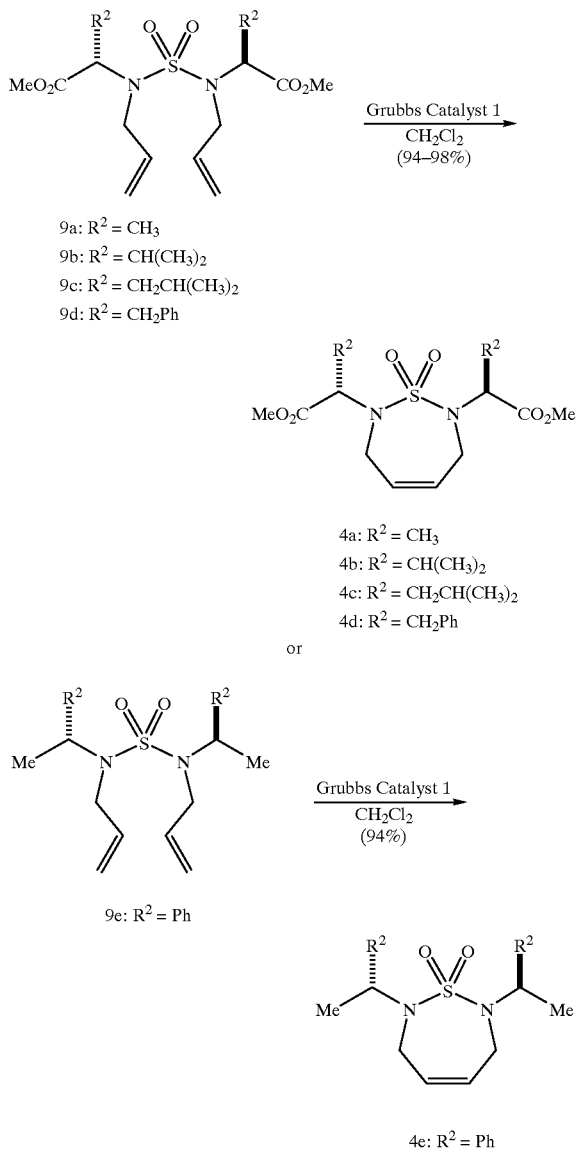

9a: $R^2 = CH_3$
9b: $R^2 = CH(CH_3)_2$
9c: $R^2 = CH_2CH(CH_3)_2$
9d: $R^2 = CH_2Ph$

4a: $R^2 = CH_3$
4b: $R^2 = CH(CH_3)_2$
4c: $R^2 = CH_2CH(CH_3)_2$
4d: $R^2 = CH_2Ph$ or

9e: $R^2 = Ph$

4e: $R^2 = Ph$

I. Preparation of 2,2'-(2S,2'S)-[(2,3,6,7-Tetrahydro-1,2,7-thiadiazepine-1,1-dioxido-2,7-diyl)]-3,3'-dimethyl bis-butyric Acid Dimethyl Ester (4b)

A stirring solution of the allylated sulfamide (9b) (200 mg, 0.494 mmol) in $CH_2Cl_2$ (50 mL) in a 100 mL round-bottom flask was degassed by bubbling argon gas through the solution for 15 minutes. The Grubbs methathesis catalyst (1) (12 mg, 0.015 mmol, 3 mol%) was added, the flask was quickly fitted with a condenser containing an argon balloon, and the solution was heated to reflux for 1.5 hours. The solution was cooled to room temperature, and the flask opened to the air. $CH_2Cl_2$ (40 mL) and Celite® (5.0 g) were added, and the solution was stirred for 18 hours. The solvent was removed under reduced pressure, EtOAc (100 mL) was added, and the solution was filtered through a plug of silica. The solvent was again removed under reduced pressure to leave a crude solid. Flash chromatography ($SiO_2$, Hexanes/EtOAc) gave 181 mg (97%) of the cyclic sulfamide (4b) as a clear solid. mp=57–58° C.; TLC $R_f$=0.11 (10:1 Hexanes/EtOAc); $[\alpha]^{25}_D$=−114.7 (c=1.00, $CHCl_3$); $^1$H NMR ($CDCl_3$, 400 MHZ) 5.49 (t, J=2.1 Hz, 2H), 4.17–4.12 (m, 4H), 3.65 (s, 6H), 3.65–3.60 (m, 2H), 2.17–2.11 (m, 2H), 1.02 (d, J=6.8 Hz, 6H), 0.91 (d, J=6.5 Hz, 6H); $^{13}$C NMR ($CDCl_3$, 100 MHZ) 170.7, 126.7, 65.1, 51.8, 40.4. 27.3, 19.1, 18.8; FTIR (neat) 3031, 1741, 1436, 1391, 1370, 1321, 1137, $cm^{-1}$; HRMS $(M+H)^+$ calculated for $C_{16}H_{29}N_2O_6S$ 377.1746, found 377.1748.

II. Preparation of 2,2'-(2S,2'S)-[(2,3,6,7-Tetrahydro-1,2,7-thiadiazepine-1,1-dioxido-2,7-diyl)]bis-propionic Acid Dimethyl Ester (4a)

In a procedure similar to that used for the preparation of cyclic sulfamide (4b), allylated sulfamide (9a) (250 mg, 0.717 mmol) was subjected to ring-closing metathesis (RCM) conditions (reflux $CH_2Cl_2$, 3 mol % catalyst, 1.5 hours). Flash chromatography ($SiO_2$, Hexanes/EtOAc) afforded 223 mg (97%) of cyclic sulfamide (4a) as a brown oil. TLC $R_f$=0.19 (3:1 Hexanes/EtOAc); $[\alpha]^{25}_D$=−62.6 (c=0.942, $CHCl_3$); $^1$H NMR ($CDCl_3$, 400 MHZ) 5.68 (t, J=1.5 Hz, 2H), 4.76 (q, J=7.3 Hz, 2H), 4.09 (d, J=17.2 Hz, 2H), 3.73 (s, 6H), 3.68 (ddd, J=20.1, 3.2, 3.2 Hz, 2H) 1.41 (d, J=7.3 Hz, 6H); $^{13}$C NMR($CDCl_3$, 100 MHZ) 172.0, 127.8, 55.3, 52.3, 42.1, 16.1; FTIR (neat) 2989, 1741, 1457, 1313, 1174 $cm^{-1}$; HRMS $(M+H)^+$ calculated for $C_{12}H_{21}N_2O_6S$ 321.1120, found 321.1103.

III. Preparation of 2,2'-(2S,2'S)-[(2,3,6,7-Tetrahydro-1,2,7-thiadiazepine-1,1-dioxido-2,7-diyl)]-4,4'-dimethyl bis-pentanoic Acid Dimethyl Ester (4c)

In a procedure similar to that used for the preparation of cyclic sulfamide (4b), allylated sulfamide (9c) (200 mg, 0.399 mmol) was subjected to RCM conditions (reflux $CH_2Cl_2$, 3 mol % catalyst, 15 hours). Flash chromatography ($SiO_2$, Hexanes/EtOAc) and recrystallization (pentane/EtOAc) afforded 1.05 g (56%) of cyclic sulfamide (4c) as a white solid. mp=89–90° C.; TLC $R_f$=0.48 (2:1 Hexanes/EtOAc); $[\alpha]^{25}_D$=−67.3 (c=1.06, $CHCl_3$); $^1$H NMR ($CDCl_3$, 400 MHZ): 5.61 (m, 2H), 4.66 (dd, J=7.9, 6.8 Hz, 2H), 3.96–3.82 (m, 4H), 3.68 (s, 6H), 1.68–1.57 (m, 6H), 0.95 (d, J=6.1 Hz, 6H), 0.91 (d, J=6.3 Hz, 6H); $^{13}$C NMR ($CDCl_3$, 100 MHZ): 171.8, 127.4, 57.4, 52.1, 41.7, 38.9, 24.6, 22.9, 21.6; FTIR (neat) 3039, 2959, 2871, 1741, 1437, 1373, 1181 $cm^{-1}$; HRMS $(M+H)^+$ calculated for $C_{18}H_{33}N_2O_6S$ 405.2059, found 405.2033.

IV. Preparation of 2,2'-(2S,2'S)-[(2,3,6,7-Tetrahydro-1,2,7-thiadiazepine-]1,1-dioxido-2,7-diyl)] 3,3'-diphenyl bis-propionic Acid Dimethyl Ester (4d)

In a procedure similar to that used for the preparation of cyclic sulfamide (4b), allylated sulfamide (9d) (200 mg, 0.399 mmol) was subjected to RCM conditions (reflux $CH_2Cl_2$, 3 mol % catalyst, 15 hours). Flash chromatography ($SiO_2$, Hexanes/EtOAc) afforded 181 mg (96%) of cyclic sulfamide (4d) as a brown oil. TLC $R_f$=0.39 (3:1 Hex/EtOAc); $[\alpha]^{25}_D$=−55.2 (c=1.098, $CHCl_3$); $^1$H NMR ($CDCl_3$, 400 MHZ) 7.29–7.19 (m, 10H), 5.46 (t, J=1.8 Hz, 2H), 4.91 (dd, J=7.8, 7.8 Hz, 2H), 3.65–3.63 (m, 10H), 3.21 (dd, J=14.2, 7.4 Hz, 2H), 2.89 (dd, J=14.2, 8.0 Hz, 2H); $^{13}$C NMR ($CDCl_3$, 100 MHZ) 170.7, 136.0, 129.2, 128.2, 127.3, 126.8, 60.3, 52.1, 41.9, 36.4; FTIR (neat) 3030, 1739, 1653, 1604, 1497, 1356, 1170, 744, 700 cm$^{-1}$; HRMS (M+H)$^+$ calculated for $C_{24}H_{29}N_2O_6S$ 473.1746, found 473.1751.

V. Preparation of 1,1'-(1R,1'R)-[(2,3,6,7-Tetrahydro-1,2,7-thiadiazepine-1,1-dioxido-2,7-diyl)]-1,1'-diphenyl Ethane (4e)

In a procedure similar to that used for the preparation of cyclic sulfamide (4b), allylated sulfamide (9e) (100 mg, 0.260 mmol) was subjected to RCM conditions (reflux $CH_2Cl_2$, 3 mol % catalyst, 16 hours). Flash chromatography ($SiO_2$, Hexanes/EtOAc) afforded 887 mg (94%) of cyclic sulfamide (4e) as a white solid. mp=90–92° C.; TLC $R_f$=0.41 (10:1 Hex/EtOAc); $[\alpha]^{25}_D$=−94.3 (c=0.70, $CHCl_3$); $^1$H NMR ($CDCl_3$, 400 MHZ) 7.45 (d, J=7.4 Hz, 4H), 7.39–7.35 (m, 4H), 7.30–7.27 (m, 2H), 5.51 (t, J=1.3 Hz, 2H), 5.44 (q, J=7.0 Hz, 2H), 3.84 (d, J=17 Hz, 2H), 3.54 (dd, J=17.5, 2.8 Hz, 2H), 1.57 (d, J=7.1 Hz, 6H); $^{13}$C NMR ($CDCl_3$, 100 MHZ) 140.5, 128.4, 128.0, 127.4, 127.3, 56.1, 40.8, 17.7; FTIR (neat) 3029, 2978, 2931, 1602, 1496, 1451, 1382, 1300, 1177, 785, 698 cm$^{-1}$; HRMS (M+H)$^+$ calculated for $C_{20}H_{25}N_2O_2S$ 357.1637, found 357.1616.

In Parts I–V of this procedure, methylene chloride was the solvent utilized. However, toluene, benzene, chlorobenzene, dichlorobenzene, DME, and mixtures thereof are also suitable solvents. Furthermore, while Grubbs catalyst 1 was utilized, Grubbs catalysts 2 and/or 3 would work as well. Finally, while the procedure was carried out at a temperature of 40° C., temperatures of anywhere from about 15–80° C. would also be suitable.

Example 1D

In the following parts I–VII of this example, compounds 4a–4d were used to prepare various functionalized sulfamides. Scheme E depicts these compounds 4a–4d, the reaction schemes, and the resulting functionalized sulfamides.

SCHEME E

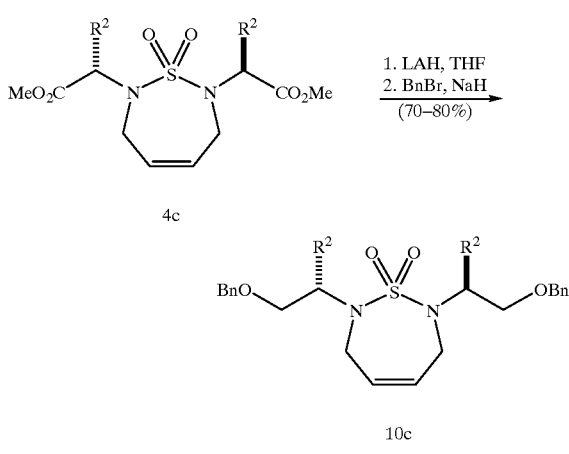

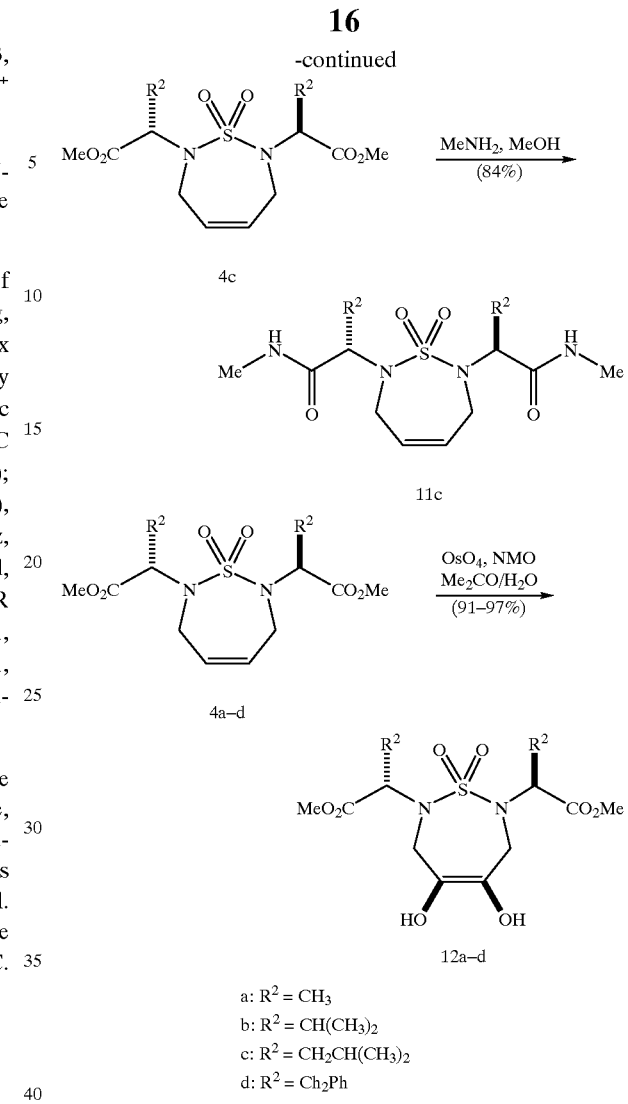

a: $R^2$ = $CH_3$
b: $R^2$ = $CH(CH_3)_2$
c: $R^2$ = $CH_2CH(CH_3)_2$
d: $R^2$ = $Ch_2Ph$

I. Preparation of 2,2'-(2,2'S)-[(2,3,6,7-Tetrahydro-1,2,7-thiadiazepine-1,1-dioxido-2,7-diyl)]-4,4'-dimethyl bis-pentanol Lithium aluminum hydride (LAH) (11 mg, 0.273 mmol) was added to a stirring solution of the cyclic sulfamide (4c) (50 mg, 0.124 mmol) in THF (8 mL) in a 25 mL round-bottom flask fitted with Argon balloon at 0° C. The reaction was stirred for 4 hours with the addition of another equivalent of LAH. $Na_2SO_4$·10$H_2O$ and several drops of distilled $H_2O$ were added until the stirred solid turned white. The mixture was filtered, and the solvent was removed under reduced pressure to give a clear oil. Purification by flash chromatography ($SiO_2$, Hexanes/EtOAc) gave 42 mg (98%) of the leucinol cyclic sulfamide as clear oil. TLC $R_f$=0.34 (1:2 Hexanes/EtOAc); $[a]^{25}_D$=−6.8 (c=0.78, $CHCl_3$); $^1$H NMR ($CDCl_3$, 400 MHZ) δ5.75 (t,J=1.8 Hz, 2H), 4.15–4.08 (m, 2H), 3.86 (d, J=17.9 Hz, 2H), 3.70 (d, J=17.9 Hz, 2H), 3.58–3.49 (m, 4H), 2.37 (s, 2H), 1.68–1.59 (m, 2H), 1.38 (ddd, J=14.3, 9.5, 4.8 Hz, 2H), 1.14 (ddd, J=14.3, 9.2, 5.0 Hz, 2H), 0.94 (d, J=6.5 Hz, 6H), 0.89 (d, J=6.7 Hz, 2H); $^{13}$C NMR ($CDCl_3$, 100 MHZ) δ128.8, 64.3, 59.5, 40.9, 38.8, 25.2, 23.7, 22.4; FTIR (neat) 3463, 2955, 2870, 1468, 1379, 1290, 1176 cm$^{-1}$; HRMS (M+H)$^+$ calculated for $C_{16}H_{33}N_2O_4S$ 349.2161, found 349.2170.

In this part of this procedure, THF was the solvent utilized. However, DME, ET$_2$O, methylene chloride, MeOH, EtOH, and mixtures thereof are also suitable solvents. Furthermore, while the reducing agent utilized was LAH, the following reducing agents would work as well: diisobutylaluminum hydride (DIBAL), AlH$_3$, LiAlH$_2$(OCH$_2$CH$_2$OCH$_3$)$_2$, LaAlH(OC(CH$_3$)$_3$)$_3$, LiH$_3$AlO$^t$Bu; LiBH$_4$; and NaBH$_4$.

II. Preparation of 1,1'-bis(benzyloxy)-2,2'-(2S,2'S)-[(2,3,6,7-Tetrahydro-1,2,7-thiadiazepine-1,1-dioxido-2,7-diyl)]-4,4'-dimethyl bis-pentane (10c)

Sodium hydride (8 mg, 0.336 mmol) was added to a stirring solution of the leucinol sulfamide prepared in Part I of this example (39 mg, 0.112 mmol) in THF (10 mL) at 0° C. The mixture stirred for 45 min and benzyl bromide (57 mg, 0.336 mmol) was added. After stirring for 12 hours at room temperature, EtOAc (20 mL) was added and the mixture was washed with 10% NaHSO$_4$, NaHCO$_3$, brine, and dried (MgSO$_4$). The solution was filtered and the solvent removed under reduced pressure. Purification by flash chromatography (SiO$_2$, Hexanes/EtOAc) gave 48 mg (81%) of sulfamide (10c) as a clear oil. TLC R$_f$=0.78(1:2 Hexanes/EtOAc); [α]$^{25}{}_D$=−11.5 (c=0.66, CHCl$_3$); $^1$H NMR (CDCl$_3$, 400 MHz) 7.36–7.27 (m, 10H), 5.57 (s, 2H), 4.51 (d, J=11.9 Hz, 2H), 4.44 (d, J=11.9 Hz, 2H), 4.31 (m, 2H), 4.07 (d, J=17.3 Hz, 2H), 3.59 (dd, J=19.2, 2.1 Hz, 2H), 3.46 (d, J=5.4 Hz, 4H), 1.73–1.65 (m, 2H), 1.50 (ddd, J=14.3, 10.0, 4.6 Hz, 2H), 1.27 (dd, J=14.2, 9.3, 5.0 Hz, 2H), 0.98 (d, J=6.5 Hz, 6H), 0.93 (d, J=6.7 Hz, 6H); $^{13}$C NMR (CDCl$_3$, 100 MHz) 138.1, 128.3, 127.9, 127.6, 127.5, 72.9, 72.5, 55.5, 40.4, 38.5, 24.6, 23.4, 21.9; FTIR (neat) 3033, 2955, 2867, 1496, 1453, 1386, 1366, 1301, 1183, 734, 698 cm$^{-1}$; HRMS (M+H)$^+$ calculated for C$_{30}$H$_{45}$N$_2$O$_4$S 529.3100, found 529.3082.

In this part of this procedure, THF was the solvent utilized. However, methylene chloride, DME, Et$_2$O, dimethyl formamide (DMF), and mixtures thereof are also suitable solvents. Furthermore, while BnBr and NaH were used as the benzylating agent and base, respectively, other suitable combinations include the following: BnBr with NaI, KH, and/or potassium hexamethyldisilazide (KHMDS) or lauric diethanolamide (LDA); BnCl with NaI, KH, and/or KHMDS; and CCl$_3$CN and KH with BnOH and tosic acid (TfOH).

III. Preparation of N,N'-dimethyl-[2,2'-(2S,2'S)-[(2,3,6,7-Tetrahydro-1,2,7-thiadiazepine-]1,1-dioxido-2,7-diyl)]]-4,4'-dimethyl bis-pentanamide (11c)

A 10 mL round-bottom flask was charged with the leucine derived cyclic sulfamide (4c) (25 mg, 0.062 mmol) and MeNH$_2$ (39 mg, 1.24 mmol) in MeOH. The mixture was stirred under argon balloon for 5 days with the addition of two more equivalents of MeNH$_2$. The solvent was removed, and the crude oil was purified by flash chromatography (SiO$_2$, 4:1 Hexanes/EtOAc) to give 21 mg (84%) of(11c) as a clear oil. TLC R$_f$=0.23 (1:2 Hexanes/EtOAc); [α]$^{25}{}_D$=−158.5 (c=0.26, CHCl$_3$); $^1$H NMR (CDCl$_3$, 400 MHZ) 6.41 (d, J=3.8 Hz, 2H), 5.69–5.68 (m, 2H), 4.41 (dd, J=9.1, 5.4 Hz, 2H), 4.05 (d, J=16.8 Hz, 2H), 3.61 (ddd, J=17.0, 4.5, 1.1 Hz, 2H), 2.82 (d, J=4.8 Hz, 6H), 1.84 (ddd, J=14.2, 8.8, 5.4 Hz, 2H), 1.66–1.57 (m, 2H) 1.48 (ddd, J=14.1, 9.1, 4.9 Hz, 2H), 0.95 (d, J=6.5 Hz, 6H), 0.91 (d, J=6.6 Hz, 6H); $^{13}$C NMR (CDCl$_3$, 100 MHZ) 170.8, 127.4, 59.2, 42.4, 38.2, 26.6, 24.8, 23.0, 21.7; FTIR (neat) 3381, 3317, 2958, 2870, 1662, 1544, 1456, 1368, 1300, 1179 cm$^{-1}$; HRMS (M+H)$^+$ calculated for C$_{18}$H$_{35}$N$_4$O$_4$S 403.2379, found 403.2406.

While MeNH$_2$ and MeOH were utilized in this part of this procedure, other suitable combinations include: R$^1$NH$_2$ and MeOH; R$^1$NH$_2$ and EtOH; and R$^1$NH$_2$ and isopropanol (iPrOH), acetonitrile, or acetone. In each of these instances R$^1$ can be hydrogen, branched and unbranched alkyl groups (preferably C$_1$–C$_{18}$, more preferably C$_1$–C$_8$), branched and unbranched alkenyl groups (preferably C$_2$–C$_{18}$, more preferably C$_2$–C$_8$), branched and unbranched alkynyl groups (preferably C$_2$–C$_{18}$, more preferably C$_2$–C$_8$), allyl groups, acyl groups (preferably C$_1$–C$_{18}$, more preferably C$_1$–C$_8$), aryl groups (preferably C$_6$–C$_{12}$), 2–15 mer peptides, and benzyl groups.

IV. Preparation of 2,2'-(2S,2'S)-[(2,3,6,7-Tetrahydro-1,2,7-thiadiazepine-(4R),(5S)-dihydroxy-1,1-dioxido-2,7-diyl)]-4,4'-dimethyl bis-pentanoic Acid Dimethyl Ester (12c)

To a stirring solution of the cyclic sulfamide (4c) (50 mg, 0.123 mmol) in a mixture of acetone (3 mL) and distilled water (1 mL) was added N-methyl morpholine N-Oxide (32 mg, 0.248 mmol), and the mixture was stirred for 15 minutes. A 0.5 M aqueous solution of OsO$_4$ (1 mg, 4 μmol) was then added. After 19 hours, Na$_2$SO$_3$ (50 mg, 0.31 mmol) was added to destroy the OsO$_4$. The mixture was filtered and concentrated to 1.5 mL under reduced pressure. Flash chromatography (SiO$_2$, 1:2 Hexanes/EtOAc) gave 50 mg (92%) of (12c) as a clear oil. TLC R$_f$=0.58 (1:2 Hexanes/EtOAc); [α]$^{25}{}_D$=−21.9 (c=0.64, CHCl$_3$); $^1$H NMR (CDCl$_3$, 400 MHZ) 4.28 (dd, J=9.3, 5.8 Hz, 1H), 4.21 (dd, J=10.6, 4.6 Hz, 1H), 3.92 (t, J=4.6, 1H), 3.83–3.73 (m, 2H), 3.79 (s, 3H), 3.76 (s, 3H), 3.65 (dd, J=15.5, 8.9 Hz, 1H), 3.40, (d, J=12.4 Hz, 1H), 3.35 (dd, J=15.6, 6.9 Hz, 1H), 1.97, (ddd, J=13.8, 10.3, 3.3 Hz, 1H), 1.83–1.72 (m, 5H), 0.97 (d, J=6.3 Hz, 3H), 0.97 (d, J=6.6 Hz, 3H), 0.96 (d, J=6.2 Hz, 3H), 0.94 (d, J=6.3 Hz, 3H); $^{13}$C NMR (CDCl$_3$, 100 MHZ) 174.2, 173.8, 69.4, 69.0, 61.6, 59.2, 53.1, 52.8, 48.8, 46.1, 39.2, 38.8, 24.7, 24.7, 23.2, 22.9, 21.6, 21.5; FTIR(neat) 3432, 1740, 1457, 1437, 1380, 1311, 1168 cm$^{-1}$; HRMS (M+H)$^+$ calculated for C$_{18}$H$_{35}$N$_2$O$_8$S 439.2114, found 439.2132.

V. Preparation of 2,2'-(2S,2'S)-[(2,3,6,7-Tetrahydro-1,2,7-thiadiazepine-(4R),(5S)-dihydroxy-1,1-dioxido-2,7-diyl)] bis-propionic Acid Dimethyl Ester (12a)

In a procedure similar to that used for the preparation of diol (12c), the cyclic sulfamide (4a) (100 mg, 0.41 mmol) was subjected to standard osmylation procedures (3 mol % OsO$_4$, NMO, 4:1 acetone/H$_2$O, 12 hours). Flash chromatography (SiO$_2$, Hexanes/EtOAc) afforded 75 mg (53%) of sulfamide (12a) as a clear oil. TLC R$_f$=0.09(1:2 Hexanes/EtOAc); [α]$^{25}{}_D$=−5.52 (c=1.36, CHCl$_3$); $^1$H NMR (CDCl$_3$, 400 MHZ) 4.35 (q, J=7.3 Hz, 1H), 4.23(q, J=7.3 Hz, 1H), 3.88 (t, J=4.6 Hz, 1H), 3.80–3.72 (m, 2H), 3.77 (s, 3H), 3.75 (s, 3H), 3.66 (dd, J=15.6, 8.9 Hz, 1H), 3.37 (d, J=15.6 Hz, 1H), 3.35 (dd,J=15.6,3.1 Hz, 1H), 1.56 (d,J=7.3 Hz, 3H), 1.53 (d,J=7.4 Hz, 3H); $^{13}$C NMR (CDCl$_3$, 100 MHZ) 173.9, 173.6, 69.4, 68.9, 58.8, 56.5, 53.0, 52.8, 48.3, 45.8, 16.3, 15.8; FTIR (neat) 3489, 3400, 2998, 1743, 1457, 1382, 1307, 1171 cm$^{31}$ $^1$; HRMS (M+H)$^+$ calculated for C$_{12}$H$_{23}$N$_2$O$_8$S 355.1175, found 355.1161.

VI. Preparation of 2,2'-(2S,2'S)-[(2,3,6,7-Tetrahydro-1,2,7-thiadiazepine-(4R),(5S)-dihydroxy-1,1-dioxido-2,7-diyl)]-3,3'-dimethyl bis-butyric Acid Dimethyl Ester (12b)

In a procedure similar to that used for the preparation of diol (12c), the cyclic sulfamide (4b) (66 mg, 0.18 mmol) was subjected to standard osmylation procedures (3 mol % OsO$_4$, NMO, 4:1 acetone/H$_2$O, 12 hours). Flash chromatography (SiO$_2$, Hexanes/EtOAc) afforded 69 mg (96%) of sulfamide (12b) as a clear solid. TLC R$_f$=0.33 (1:2 Hexanes/EtOAc); [α]$^{25}_D$=−32.7 (c=0.92, CHCl$_3$); $^1$H NMR (CDCl$_3$, 400 MHZ) 3.94 (d, J=10.1 Hz, 1H), 3.92–3.83 (m, 2H), 3.86 (d, J=10.6 Hz, 1H), 3.76 (s, 3H), 3.74 (s, 3H), 3.59–3.36 (m, 4H), 2.31–2.23 (m, 1H), 2.23–2.14 (m, 1H) 1.04 (d, J=6.6 Hz, 6H), 0.97 (d, J=6.4 Hz, 3H), 0.97 (d, J=6.5 Hz, 3H); $^{13}$C NMR (CDCl$_3$, 100 MHZ) 173.1, 172.6, 70.0, 69.5, 67.9, 66.0, 52.5, 52.3, 47.4, 45.3, 28.5, 28.3, 20.0, 20.0, 19.6, 19.5; FTIR (neat) 3457, 1740, 1436, 1380, 1311, 1158 cm$^{-1}$; HRMS (M+H)$^+$ calculated for C$_{16}$H$_{31}$N$_2$O$_8$S 411.1801, found 411.1809.

VII. Preparation of 2,2'(2S,2'S)-[(2,3,6,7-Tetrahydro-1,2,7-thiadiazepine-(4R),(5S)-dihydroxy-1,1-dioxido-2,7-diyl)]-3,3'-diphenyl bis-propionic Acid Dimethyl Ester (12d)

In a procedure similar to that used for the preparation of diol (12c), the cyclic sulfamide (4d) (104 mg, 0.217 mmol) was subjected to standard osmylation procedures (3 mol % OsO$_4$, NMO, 4:1 acetone/H$_2$O, 12 hours). Flash chromatography (SiO$_2$, Hexanes/EtOAc) afforded 110 mg (97.2%) of sulfamide (12d) as a white solid. mp=153–154° C.; TLC R$_f$=0.20 (1:1 Hexanes/EtOAc); [α]$^{25}_D$=131.8 (c=0.22, CHCl$_3$); $^1$H NMR (CDCl$_3$, 400 MHZ) 7.38–7.21 (m, 10H), 4.36 (dd, J=10.3, 5 Hz, 1H), 4.13 (dd, J=10.6, 4.1 Hz, 1H), 3.78 (s, 3H), 3.75 (s, 3H), 3.62–3.53 (nfom, 4H), 3.45 (dd, J=14.7, 5 Hz, 1H), 3.39 (dd, J=14.4, 4.1 Hz, 1H), 3.23 (dd, J=14.4, 10.6 Hz, 1H), 3.12 (dd, J=14.7, 10.4 Hz, 1H), 2.62 (d, J=12.7 Hz, 1H), 2.52 (dd, J=16.0, 4.6 Hz, 1H); $^{13}$C NMR(CDCl$_3$, 100 MHZ) 173.7, 171.0, 137.0, 136.5, 129.5, 129.2, 128.6, 128.5, 127.0, 126.9, 69.8, 68.3, 68.0, 63.7, 53.6, 52.6, 51.4, 47.0, 36.9, 36.6; FTIR(neat) 3502, 3382, 3029, 1741, 1716, 1604, 1559, 1497, 1312, 1153, 753, 702 cm$^{-1}$; HRMS (M+H)$^+$ calculated for C$_{24}$H$_{31}$N$_2$O$_8$S 507.1801, found 507.1806.

While OsO$_4$, NMO, and Me$_2$CO/H$_2$O were utilized in Parts IV–VII of this procedure, other suitable combinations include: OsO$_4$, NMO, and Me$_2$CO; and OsO$_4$, NMO, and tBuOH/H$_2$O.

Example 2

The overall reaction scheme followed in Examples 2A–2B below is set forth in Scheme F.

Scheme F

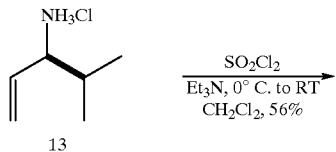

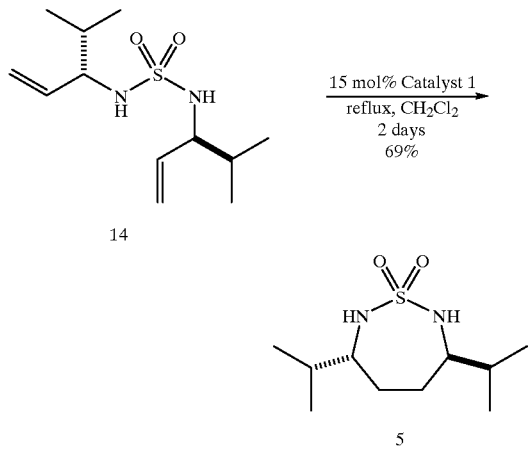

Example 2A

In this example, compound (13) was used to prepare N,N'-Sulfonyl-(3S,3'S)-bis(4-methyl-1-penten-3-amine) (14). Scheme G depicts these compounds and the reaction in this portion.

Scheme G

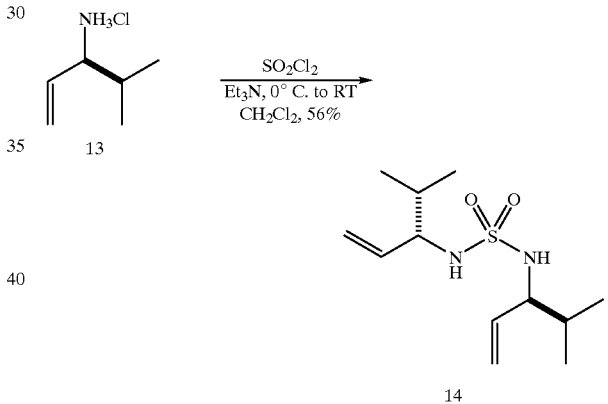

In a procedure similar to the preparation of the sulfamide (8b), valine-derived allylic amine hydrochloride salt (13) (250 mg, 1.84 mmol) was subjected to sulfamide formation conditions (SO$_2$Cl$_2$, Et$_3$N, CH$_2$Cl$_2$ 0° C.-RT, 8 hours). Flash chromatography (SiO$_2$, Hexanes/EtOAc) yielded 128 mg (56%) of sulfamide (14) as a white solid. mp=51–52° C.; TLC R$_f$=0.48 (3:1 Hexanes/EtOAc); [α]$^{25}_D$=85.9 (c=0.51, CHCl$_3$); $^1$H NMR (CDCl$_3$, 400 MHz) 5.70 (ddd, J=17.7, 10.3, 7.8 Hz, 2H), 5.25 (dd, J=17, 0.9 Hz, 2H), 5.21 (d, J=10.2 Hz, 2H), 4.29 (d, J=7.7 Hz, 2H), 3.65 (dd, J=7.8, 5.4 Hz, 2H), 1.84 (m, 2H), 0.92 (d, J=6.9 Hz, 6H), 0.89 (d, J=6.8 Hz, 6H); $^{13}$C NMR (CDCl$_3$, 100 MHz) 136.5, 117.5, 62.3, 32.4, 18.6, 17.8; FTIR (neat) 3290, 2962, 2939, 2875, 1652, 1568, 1456, 1436, 1369, 1316, 1157 cm$^{-1}$; HRMS (M+H)$^+$ calculated for C$_{12}$H$_{25}$N$_2$O$_2$S 261.1637, found 261.1646.

In this example, methylene chloride was the solvent utilized. However, acetonitrile, chloroform, toluene, benzene, chlorobenzene, dichlorobenzene, THF, diethyl ether, acetone, DME, and mixtures thereof are also suitable solvents. Furthermore, while Et₃N was used as the base, other bases which could be used included pyridine, NaHCO₃, Na₂CO₃, K₂CO₃, NaH, KH, any tertiary amine, and mixtures thereof. Finally, while the procedure was carried out at temperatures of 0–20° C., temperatures of anywhere from about −20–20° C. would also be suitable.

Example 2B

In this example, N,N'-Sulfonyl-(3S,3'S)-bis(4-methyl-1-penten-3-amine) (14) was used to prepare (3S,6S)-[(2,3,6,7-Tetrahydro-3,6-bis(methylethyl)-1,2,7-thiadiazepine-1,1-dioxide (5). Scheme H depicts these compounds and the reaction in this portion.

Scheme H

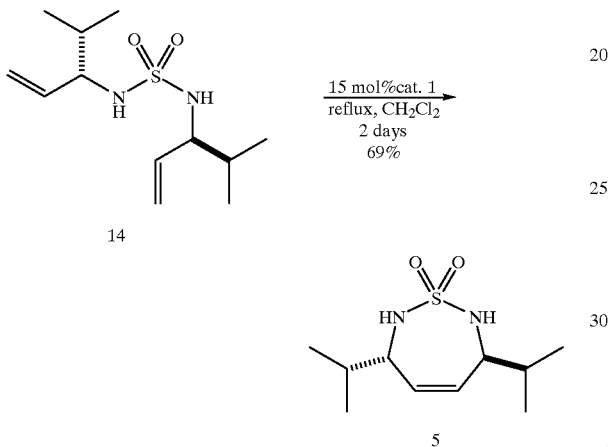

14

5

In a procedure similar to that used for the preparation of cyclic sulfamide (4b), sulfamide (14) (50 mg, 0.192 mmol) was subjected to RCM conditions (reflux $CH_2Cl_2$, 3 mol % catalyst, 15 hours). Flash chromatography ($SiO_2$, Hexanes/EtOAc) afforded 31 mg (69%) of cyclic sulfamide (5) as a white solid. mp=152–153° C.; TLC $R_f$=0.35 (3:1 Hex/EtOAc); $[\alpha]^{25}_D$=50.0 (c=0.18, $CHCl_3$); ¹H NMR ($CDCL_3$, 400 MHz) 5.59 (s, 2H), 4.94 (d, J=10.7 Hz, 2H), 3.98 (dd, J=8.2, 4.0 Hz, 2H), 1.92–1.87 (m, 2H), 0.99 (d, J=6.7 Hz, 6H), 0.92 (d, J=6.9 Hz, 6H); ¹³C NMR ($CDCl_3$, 100 MHz) 133.1, 56.3, 32.6, 18.7, 17.1; FTIR (neat) 3303, 3257, 2959, 2931, 2875, 1653, 1559, 1321, 1161 cm⁻¹; HRMS (M+H)⁺ calculated for $C_{10}H_{21}N_2O_2S$ 233.1324, found 233.1321.

In this example, methylene chloride was the solvent utilized. However, toluene, benzene, chlorobenzene, dichlorobenzene, DME, and mixtures thereof are also suitable solvents. Furthermore, while Grubbs catalyst 1 was utilized, Grubbs catalyst 2 and/or 3 could be utilized as well. Finally, while the procedure was carried out at temperatures of 40° C., temperatures of anywhere from about 15–80° C. would also be suitable.

Example 3

The overall reaction scheme followed in Examples 3A–3H below is set forth in Scheme I. Each step of this scheme is described in detail in Examples 3A–3H.

Scheme I

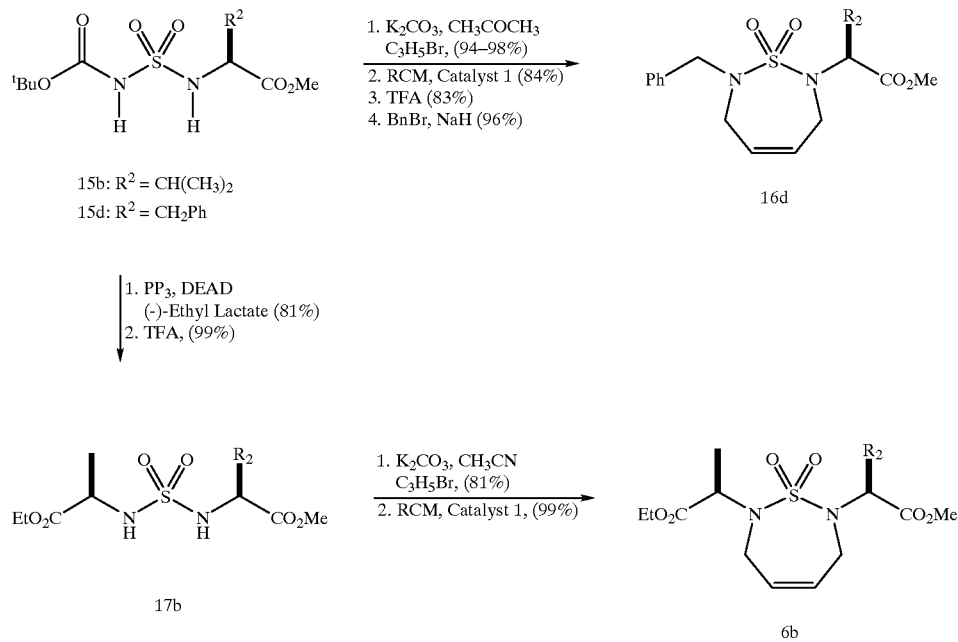

Example 3A

In this example, compound (15d) was used to prepare N,N'-bis(2-propenyl)-N-(tert-butoxycarbonylsulfonyl) L-phenylalanine methyl ester. Scheme J depicts these compounds and the reaction in this portion.

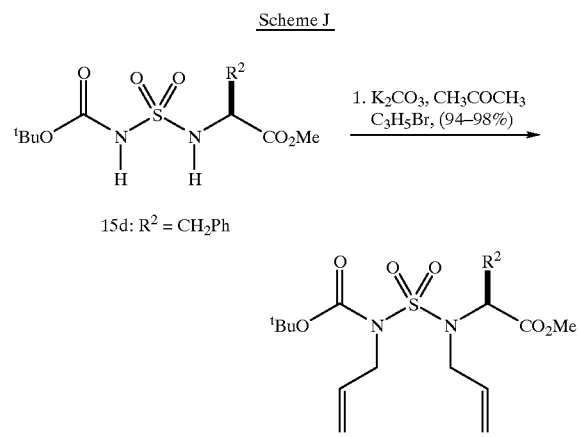

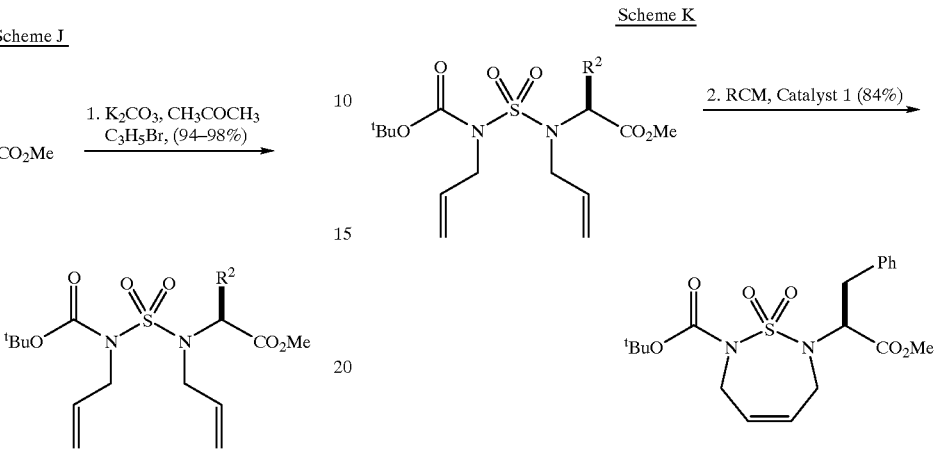

Anhydrous $K_2CO_3$ (0.771 g, 5.58 mmol) and allyl bromide (0.507 mL, 0.709 g, 5.86 mmol) were added to a stirring solution of (15d) (0.500 g, 1.40 mmol) in dry acetone (14 mL) in an oven-dried 50 mL round-bottom flask. The mixture was heated to reflux under argon for 12 hours. The solution was then cooled, suction filtered, and the solvent removed under reduced pressure to give a pale yellow oil. Flash chromatography ($SiO_2$, 4:1 Hexane:EtOAc) yielded 504 mg (82%) of a clear, colorless oil. TLC $R_f$=0.35 (4:1 Hexanes/EtOAc); $[\alpha]^{25}_D$=-27.2 (c=1.00, $CHCl_3$); $^1H$ NMR ($CDCl_3$, 400 MHz) δ7.31–7.21 (m, 5H), 5.98–5.82 (m, 2H), 5.28 (ddd J=15.8, 3.6, 1.5 Hz, 2H), 5.17 (ddd, J=10.3, 5.1, 1.3 Hz, 2H), 4.83 (dd, J=9.0, 6.2 Hz, 1H), 5.28 (ddd J=15.8, 3.5, 1.5 Hz, 2H), 5.17 (ddd J=9.2, 5.1, 1.3 Hz, 2H), 4.32 (dd J=9.0, 6.2Hz, 1H), 4.22 (m, 3H), 4.12 (dd, J=16.6, 6.8 Hz, 1H), 3.62 (s, 3H), 3.26 (dd J=13.6, 9.0 Hz, 1H), 3.05 (dd J=13.6, 6.2 Hz, 1H), 1.51 (s, 9H); $^{13}C$ NMR ($CDCl_3$, 100 MHz) 171.3, 151.6, 136.9, 135.5, 133.6, 129.7, 128.9, 127.3, 118.0, 117.9, 84.0, 62.1, 52.4, 51.6, 50.0, 37.5, 28.5; FTIR (neat) 3082, 2980, 1731, 1644, 1605, 1494, 1442, 1371, 1319, 1249, 1149, 1036 $cm^{-1}$; HRMS $(M+H)^+$ calculated for $C_{21}H_{30}N_2O_6S$ 439.1903, found 439.1882.

In this example, acetone was the solvent utilized. However, acetonitrile, chloroform, toluene, benzene, chlorobenzene, dichlorobenzene, THF, diethyl ether, methylene chloride, DME, and mixtures thereof are also suitable solvents. Furthermore, while $K_2CO_3$ was used as the base, other bases which could be used include pyridine, $NaHCO_3$, $Na_2CO_3$, NaH, KH, and mixtures thereof. The allylating agent utilized was allyl bromide, but the following would work as well: allyl iodide; allyl bromide, NaI; allyl bromide, KI; and allyl bromide, $Bu_4NI$. Finally, while the procedure was carried out at temperatures of 56° C. or 82° C., temperatures of anywhere from about 40–100° C. would also be suitable.

Example 3B

In this example, N,N'-bis(2-propenyl)-N-(tert-butoxycarbonylsulfonyl) L-phenylalanine methyl ester was used to prepare 2-(2S)-[(2,3,6,7-Tetrahydro-1,2,7-thiadiazepine-1,1-dioxido-7-tert-butyloxycarbonyl-2-yl)] 3-phenyl-propionic acid methyl ester. Scheme K depicts these compounds and the reaction in this portion.

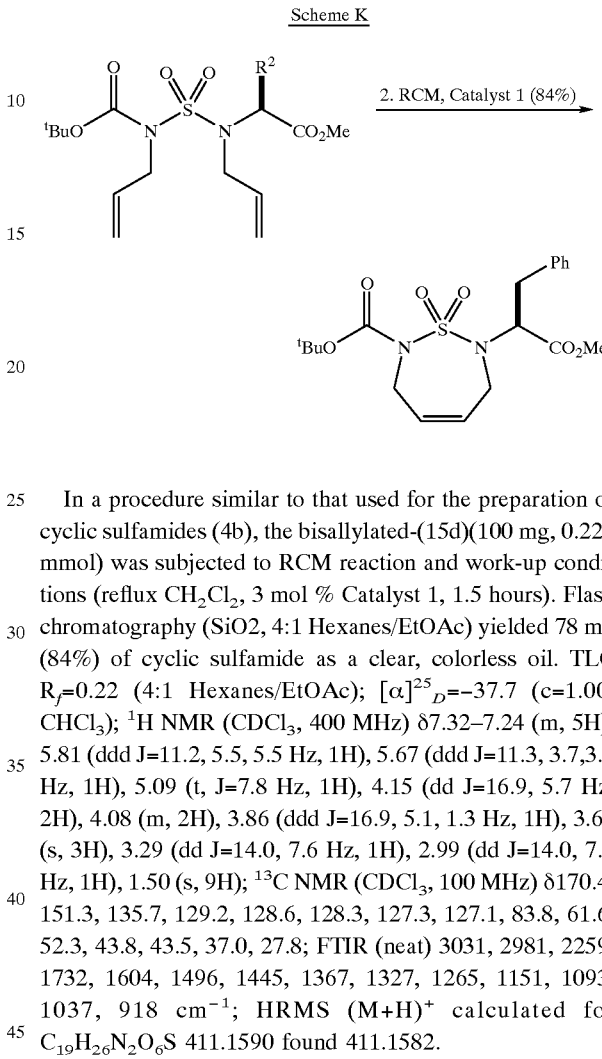

In a procedure similar to that used for the preparation of cyclic sulfamides (4b), the bisallylated-(15d)(100 mg, 0.228 mmol) was subjected to RCM reaction and work-up conditions (reflux $CH_2Cl_2$, 3 mol % Catalyst 1, 1.5 hours). Flash chromatography (SiO2, 4:1 Hexanes/EtOAc) yielded 78 mg (84%) of cyclic sulfamide as a clear, colorless oil. TLC $R_f$=0.22 (4:1 Hexanes/EtOAc); $[\alpha]^{25}_D$=-37.7 (c=1.00, $CHCl_3$); $^1H$ NMR ($CDCl_3$, 400 MHz) δ7.32–7.24 (m, 5H), 5.81 (ddd J=11.2, 5.5, 5.5 Hz, 1H), 5.67 (ddd J=11.3, 3.7,3.7 Hz, 1H), 5.09 (t, J=7.8 Hz, 1H), 4.15 (dd J=16.9, 5.7 Hz, 2H), 4.08 (m, 2H), 3.86 (ddd J=16.9, 5.1, 1.3 Hz, 1H), 3.68 (s, 3H), 3.29 (dd J=14.0, 7.6 Hz, 1H), 2.99 (dd J=14.0, 7.9 Hz, 1H), 1.50 (s, 9H); $^{13}C$ NMR ($CDCl_3$, 100 MHz) δ170.4, 151.3, 135.7, 129.2, 128.6, 128.3, 127.3, 127.1, 83.8, 61.6, 52.3, 43.8, 43.5, 37.0, 27.8; FTIR (neat) 3031, 2981, 2259, 1732, 1604, 1496, 1445, 1367, 1327, 1265, 1151, 1093, 1037, 918 $cm^{-1}$; HRMS $(M+H)^+$ calculated for $C_{19}H_{26}N_2O_6S$ 411.1590 found 411.1582.

In this example, methylene chloride was the solvent utilized. However, toluene, benzene, chlorobenzene, dichlorobenzene, DME, and mixtures thereof are also suitable solvents. Furthermore, while Grubbs catalyst 1 was utilized, Grubbs catalyst 2 and/or 3 could be utilized as well. Finally, while the procedure was carried out at temperatures of 40° C., temperatures of anywhere from about 15–80° C. would also be suitable.

Example 3C

In this example, the 2-(2S)-[(2,3,6,7-Tetrahydro-1,2,7-thiadiazepine-1,1-dioxido-7-tert-butyloxycarbonyl-2-yl)]3-phenyl-propionic acid methyl ester prepared in Example 3B was used to prepare 2-(2S)-[(2,3,6,7-Tetrahydro-1,2,7-thiadiazepine-1,1-dioxido-2-yl)] 3-phenyl-propionic acid methyl ester. Scheme L depicts these compounds and the reaction in this portion.

Scheme L

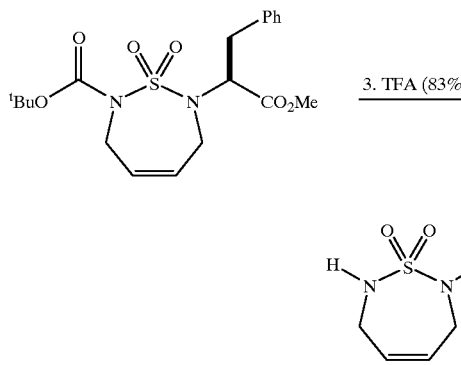

Scheme M

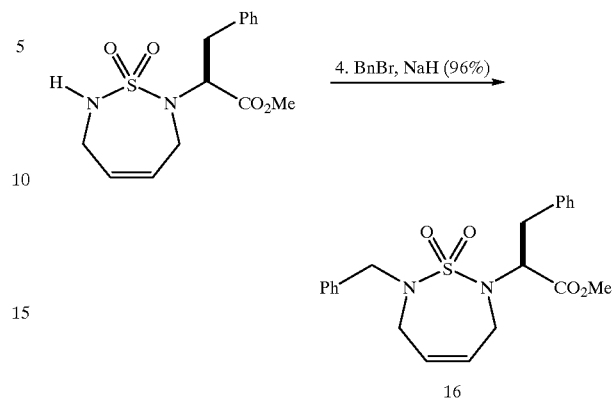

16

The Boc-protected cyclic sulfamide prepared in Example 3B (50 mg, 0.122 mmol) was added to an oven-dried 5 mL round-bottom flask, followed by trifluoroacetic acid (TFA) (194 mg, 0.131 mL, 1.71 mmol). The solution was stirred at ambient temperature for 36 hours. $CH_2Cl_2$ (4 mL) was added and the resulting solution washed with saturated $NaHCO_3$ (3 times). The aqueous solution was back-extracted with methylene chloride (2 times), and the combined organic solutions washed with water, brine, and dried $Na_2SO_4$. The solution was suction filtered, and the solvent removed under reduced pressure. Flash chromatography ($SiO_2$, 2:1 Hexanes/EtOAc) yielded 31.2 mg (83%) of a white crystalline solid. mp=62–64° C.; TLC $R_f$=0.20 (2:1 Hexanes/EtOAc); $[\alpha]^{25}_D$=−59.85 (c=1.00, $CHCl_3$); $^1H$ NMR ($CDCl_3$, 400 MHz) $\delta$7.31–7.21 (m, 5H), 5.73–5.65 (m, 1H), 5.64–5.57 (m, 1H), 4.97 (dd J=8.0, 5.7 Hz, 1H), 4.86(dd J=8.9, 6.8 Hz, 1H), 4.04 (ddd J=8.9, 2.3, 1.7 Hz, 1H), 3.81 (ddd J=18.5, 5.1, 1.0 Hz, 1H), 3.69 (s, 3H), 3.47 (ddd J=18.0, 4.6, 1.0 Hz, 1H), 3.44–3.34 (m, 1H), 3.29 (dd J=26.1, 6.8 Hz, 1H), 2.96 (dd J=14.3, 8.9 Hz, 1H); $^{13}C$ NMR($CDCl_3$, 100 MHz) $\delta$171.0, 136.2, 129.7, 129.5, 129.2, 128.4, 128.2, 128.0, 126.9, 126.7, 61.0, 52.2, 41.9, 40.7, 36.3; FTIR (neat) 3297, 3030, 2952, 2861, 1737, 1603, 1496, 1437, 1348, 1318, 1238, 1161, 1095, 983, 917, 887 $cm^{-1}$; HRMS (M+H)$^+$ calculated for $C_{14}H_{18}N_2O_4S$ 311.1066 found 311.1060.

Other suitable solvents which could be utilized in this preparation procedure include: methylene chloride, THF, ether, acetonitrile, benzene, and mixtures thereof. Furthermore, while TFA was utilized as the acid, $NaHSO_4$ and HCl could be utilized as well. Finally, while the procedure was carried out at room temperature, temperatures of anywhere from about 0–80° C. would also be suitable.

Example 3D

In this example, 2-(2S)-[(2,3,6,7-Tetrahydro-1,2,7-thiadiazepine-1,1-dioxido-2-yl)]3-phenyl-propionic acid methyl ester prepared in Example 3C was used to prepare 2-(2S)-[(2,3,6,7-Tetrahydro-1,2,7-thiadiazepine-1,1-dioxido-7-benzyl-2-yl)]3-phenyl-propionic acid methyl ester (16). Scheme M depicts these compounds and the reaction in this portion.

Anhydrous $K_2CO_3$ (44 mg, 0.318 mmol) and benzyl bromide (40 μL, 0.057 g, 0.334 mmol) were added to a stirring solution of the cyclic sulfamide prepared in Example 3C (49 mg, 0.159 mmol) in dry $CH_3CN$ (1.5 ml), in an oven dried 5 mL round-bottom flask. The solution was heated to 55° C. and stirred for 36 hours, cooled to room temperature, and diluted with $CH_2Cl_2$ (3 mL). The solution was filtered, and the solvent removed under reduced pressure. Flash chromatography ($SiO_2$, 4:1 Hexanes/EtOAc) yielded 62 mg (96%) of sulfamide (16) as a white crystalline solid. mp=56–58° C.; TLC $R_f$=0.26 (4:1 Hexanes/EtOAc); $[\alpha]^{25}_D$=−36.8 (c=1.00, $CHCl_3$); $^1H$ NMR($CDCl_3$, 400 MHz) $\delta$7.33–7.20 (m, 10H), 5.83 (ddd J=10.9, 4.4, 1.3 Hz, 1H), 5.45 (ddd J=9.8, 5.3, 4.4 Hz, 1H), 4.97 (dd J=9.3, 6.4 Hz, 1H), 4.03 (s, 2H), 3.98 (ddd J=18.2, 4.0,2.0 Hz, 1H), 3.76 (dd J=18.2, 5.8 Hz, 1H), 3.73 (s, 3H), 3.53 (dd J=17.8 3.9 Hz, 1H), 3.38 (d, 2.4 Hz, 1H), 3.32 (dd J=14.3, 6.4 Hz, 1H), 2.95 (dd J=18.2, 8.9 Hz, 1H); $^{13}C$ NMR($CDCl_3$, 100 MHz) $\delta$171.2, 136.4, 136.1, 129.5, 128.8, 128.5, 128.4, 128.1, 127.7, 127.3, 126.9, 61.4, 52.3, 51.1, 43.5, 41.6, 36.6; FTIR (neat) 3065, 3026, 2951, 1740, 1603, 1498, 1451, 1439, 1354, 1320, 1160, 1099, 926, 753 $cm^{-1}$; HRMS (M+H)$^+$ calculated for $C_{21}H_{24}N_2O_4S$ 401.1535 found 401.1556.

In this example, THF was the solvent utilized. However, methylene chloride, DME, $Et_2O$, DMF, and mixtures thereof are also suitable solvents. Furthermore, while BnBr and NaH were used as the benzylating agent and base, respectively, other suitable combinations include the following: BnBr with NaI, KH, and/or KHMDS; BnCl with NaI, KH, and/or KHMDS; and $CCl_3CN$ and KH with BnOH and TfOH.

Example 3E

In this example, compound (15b) was used to prepare N-tert-butyloxycarbonyl-N'-[[(1R)-1-ethoxycarbonyl-ethylamino]sulfonyl]-L-valine methyl ester. Scheme N depicts these compounds and the reaction in this portion.

Scheme N

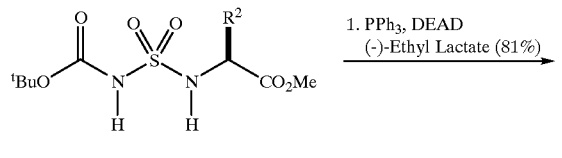

15b: R² = CH(CH₃)₂

1. PPh₃, DEAD
(-)-Ethyl Lactate (81%)

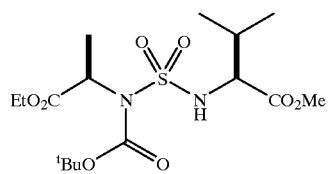

Scheme O

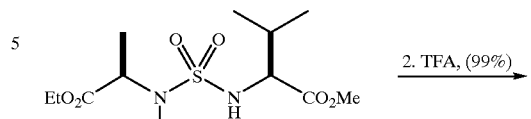

2. TFA, (99%)

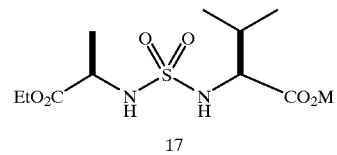

17

Diethyl azodicarboxylate (DEAD) (508 μL, 3.23 mmol) was added via dropwise addition to a stirring solution of the sulfamide (15b) (1.00 g, 3.23 mmol) in THF (2 mL). A solution consisting of (L)-(−)-Ethyl lactate (366 μL, 3.23 mmol) and PPh₃ (847 mg, 3.23 mmol) in THF (3 mL), was slowly cannulated into the sulfamide solution. After 3 hours, the reaction mixture was concentrated and dissolved in ether to precipitate Ph₃PO. The solution was filtered, and concentrated under reduced pressure to leave a crude oil. Flash chromatography (SiO₂, 5:1 Hexanes/EtOAc) yielded 1.07 g (81%) of Boc-protected sulfamide as a yellow oil. TLC $R_f$=0.63 (2:1 Hexanes/EtOAc); $[\alpha]^{25}_D$=+68.8 (c=1.00, CHCl₃); ¹H NMR (400 MHz, CDCl₃) δ6.13 (d, J=7.6 Hz, 1H), 4.89 (q, J=6.9 Hz, 1H), 4.19 (q, J=7.1 Hz, 2H), 4.09 (dd, J=7.6, 4.0 Hz, 1H), 3.77 (s, 3H), 2.18–2.15 (m, 1H), 1.57 (d, J=6.9 Hz, 3H), 1.50 (s, 9 H), 1.27 (t, J=7.1 Hz, 3H), 1.01 (d, J=6.8 Hz, 3H), 0.89 (d, J=6.9 Hz, 3H); ¹³C NMR (100 MHz, CDCl₃) δ71.15, 170.10, 150.34, 128.22, 84.82, 61.52, 61.48, 56.11, 52.29, 32.01, 27.73, 18.62, 17.14, 16.45, 14.03; FTIR (neat) 3297, 1742, 1458, 1429, 1371, 1299, 1277, 1262, 1219, 1153 cm⁻¹; HRMS (M+H)⁺ calculated for $C_{16}H_{31}N_2O_8S$ 411.1801, found 411.1784.

In this example, THF was the solvent utilized. However, methylene chloride, Et₂O, DMF, CH₃CN, benzene, and mixtures thereof are also suitable solvents. Furthermore, while Ph₃P and DEAD were used as the reagents, other suitable reagents include: polymer-bound Ph₃P; Ph₃As; diisopropyl azodicarboxylate (DIAD); ditertbutyl azocarboxylate (DTEB); and dicyclohexyl azodicarboxylate (DCAD). Finally, while the procedure was carried out at room temperature, temperatures anywhere from 0° C. to room temperature would also work.

Example 3F

In this example, the N-tert-butyloxycarbonyl-N'-[[(1R)-1-ethoxycarbonyl-ethylamino]sulfonyl]-L-valine methyl ester prepared in Example 3E was used to prepare N-[[(1R)-1-ethoxycarbonyl-ethylamino]sulfonyl]-L-valine methyl ester (17b). Scheme O depicts these compounds and the reaction in this portion.

A stirring solution of the Boc-protected sulfamide prepared in Example 3E (500 mg, 1.22 mmol) in CH₂Cl₂ (1.0 mL) was prepared and TFA (1.41 mL, 18.3 mmol) was added to this solution. After 1.5 hours, the reaction mixture was diluted with CH₂Cl₂ (15 mL) and washed with NaHCO₃ (2 times), H₂O (2 times), brine (2 times), and dried (Na₂SO₄). The organic layer was concentrated under reduced pressure. Flash chromatography (SiO₂, 1:1 Hexanes/EtOAc) yielded 380 mg (100%) of sulfamide (17) as a light yellow solid. mp=79–81° C.; TLC $R_f$=0.55 (1:1 Hexanes/EtOAc); $[\alpha]^{25}_D$=−129.2 (c=0.5, CDCl₃); ¹H NMR (400 MHz, CDCl₃) δ4.98 (t, J=10.1, 8.9 Hz, 2H), 4.22 (q, J=7.1 Hz, 2H), 4.01 (m, 1H), 3.80 (dd, J=10.2, 4.9 Hz, 1H), 3.77 (s, 3H), 2.08 (m, 1H), 1.37 (d, J=7.1 Hz, 3H), 1.26 (t, J=7.1 Hz, 3H), 0.98 (d, J=6.8 Hz, 3H), 0.88 (d, J=6.9 Hz, 3H); ¹³C NMR (100 MHz, CDCl₃) δ173.01, 172.87, 61.73, 61.09, 52.36, 51.66, 31.16, 19.20, 18.88, 17.45, 14.02; FTIR (neat) 3282, 1742, 1451, 1437, 1349, 1299, 1270, 1139 cm⁻¹; HRMS (M+H)⁺ calculated for $C_{11}H_{23}N_2O_6S$ 311.1277, found 311.1262.

Other suitable solvents which could be utilized in this preparation procedure include: methylene chloride, THF, Et₂O, CH₃CN, and mixtures thereof. Furthermore, while TFA was utilized as the acid, NaHSO₄ and HCl could be utilized as well. Finally, while the procedure was carried out at room temperature, temperatures of anywhere from about 0–80° C. would also be suitable.

Example 3G

In this example, N-[[(1R)-1-ethoxycarbonyl-ethylamino]sulfonyl]-L-valine methyl ester (17) was used to prepare N,N'-bis(2-propenyl)-N-[[(1R)-1-ethoxycarbonyl-ethylamino]sulfonyl]-L-valine methyl ester. Scheme P depicts these compounds and the reaction in this portion.

Scheme P

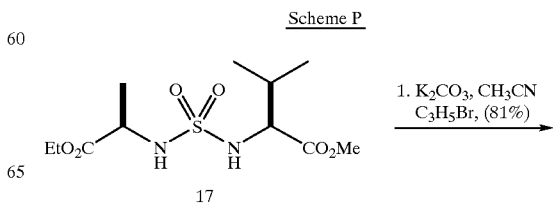

17

1. K₂CO₃, CH₃CN
C₃H₅Br, (81%)

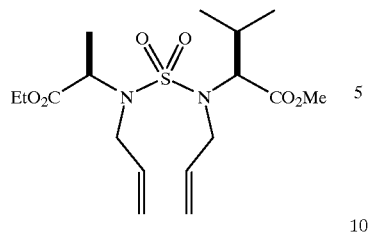

A stirring solution of sulfamide (17) (150 mg, 0.484 mmol) in CH$_3$CN (2.5 mL) in a 10 mL flame dried round-bottom flask was prepared and allyl bromide (0.105, 1.21 mmol) followed by K$_2$CO$_3$ (167 mg, 1.21 mmol) was added to this solution. The reaction was allowed to stir overnight at room temperature. The reaction mixture was washed with H$_2$O (2 times), brine (2 times), and dried (Na$_2$SO$_4$). The organic layer was concentrated under reduced pressure. Flash chromatography (SiO$_2$, 1:1 Hexanes/EtOAc) yielded 152 mg (81%) of the bis-allylated sulfamide as clear oil. TLC Rf=0.56 (2:1 Hexanes/EtOAc); $[\alpha]^{25}{}_D$=−30.2 (c=1.00, CHCl$_3$); $^1$H NMR (400 MHZ, CDCl$_3$) δ5.93 (m,2H), 5.21 (m, 2H), 5.15 (dd,J=10.2, 1.2 Hz, 1H), 5.11 (dd, J=10.1, 1.1 Hz, 1H), 4.19 (m, 3H), 4.07 (d, J=10.6 Hz, 1H), 3.99 (m 2H), 3.90 (dd, J=16.2, 6.16 Hz, 1H), 3.78 (dd, 16.1, 6.6 Hz, 1H), 3.70 (s, 3H), 2.20 (m, 1H), 1.48 (d, J=7.2 Hz, 3H), 1.28 (t, J=7.1 Hz, 3H), 1.02 (d, J=6.6 Hz, 3H), 0.92 (d, J=6.5 Hz, 3H); $^{13}$C NMR (100 MHZ, CDCl$_3$) d 171.62, 171.52, 135.12, 134.67, 118.08, 117.60, 66.25, 61.29, 55.49, 51.69, 49.02, 47.84, 28.23, 19.62, 19.56, 15.45, 14.05 ppm; FTIR (neat) 2982, 2890, 1741, 1643, 1441, 1380, 1336, 1297, 1336, 1297, 1205, 1160, 1134 cm$^{-1}$; HRMS (M+H)$^+$ calculated for C$_{17}$H$_{31}$N$_2$O$_6$S 391.1903, found 391.1879.

In this example, acetone was the solvent utilized. However, acetonitrile, chloroform, toluene, benzene, chlorobenzene, dichlorobenzene, THF, diethyl ether, methylene chloride, DME, and mixtures thereof are also suitable solvents. Furthermore, while K$_2$CO$_3$ was used as the base, other bases which could be used include pyridine, NaHCO$_3$, Na$_2$CO$_3$, NaH, KH, and mixtures thereof. The allylating agent utilized was allyl bromide, but the following would work as well: allyl iodide;

allyl bromide, NaI; allyl bromide, KI; and allyl bromide, Bu$_4$NI. Finally, while the procedure was carried out at temperatures of 56° C. or 82° C., temperatures of anywhere from about 40–100° C. would also be suitable.

Example 3H

In this example, N,N'-bis(2-propenyl)-N-[[(1R)-1-ethoxycarbonyl-ethylamino]sulfonyl]-L-valine methyl ester was used to prepare 2-(2S)-[(7-[(1'R)-1'-ethoxycarbonyl-ethyl]-2,3,6,7-Tetrahydro-1,2,7-thiadiazepine-1,1-dioxido-2-yl)] 3-phenyl propionic acid methyl ester (6). Scheme Q depicts these compounds and the reaction in this portion.

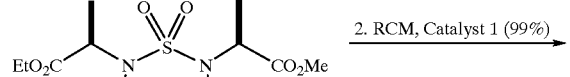

Scheme Q

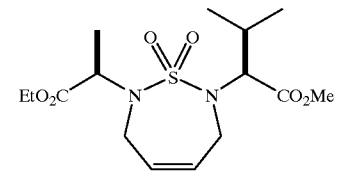

To a stirring solution of the bis-allylated sulfamide prepared in the previous experimental (60 mg, 0.153 mmol) in degassed CH$_2$Cl$_2$ in a 10 mL flame dried round-bottom flask is taken up in 3.1 mL (0.05 M). The Grubbs metathesis catalyst (6.32 mg, 0.008 mmol) was then added. After 10 minutes, the solution color changed from purple to brown. After 3 hours, TLC showed the reaction was complete. The reaction solution was then concentrated down and directly purified by column chromatography to yield 31.6 mg (67%) of the cyclic sulfamide (6) as pure brown oil. TLC R$_f$=0.37 (2:1 Hexanes/EtOAc); $[\alpha]^{25}{}_D$=−24.0 (c=0.25, CDCl$_3$); $^1$H NMR (400 MHZ, CDCl$_3$) δ5.58 (m, 2H), 4.71 (q, J=7.3, 1H), 4.18 (q, J=7.1 Hz, 2H), 4.11 (m, 3H), 3.72 (dd J=18.8, 4.9 Hz, 1H), 3.66 (s, 3H), 3.61 (dd, J=18.3,4.5 Hz, 1H), 2.14 (m, 1H), 1.39 (d, J=7.3 Hz, 3H), 1.28 (t, J=7.2 Hz, 3H), 1.01 (d, J=6.7 Hz, 3H), 0.91 (d, J=6.5 Hz, 3H); $^{13}$C NMR (100 MHZ, CDCl$_3$) d 171.52, 170.87, 127.51, 127.21, 64.87, 61.43, 55.65, 51.80, 41.67, 41.02, 27.47, 19.13, 18.90, 16.29, 14.10; FTIR(neat) 1742, 1589, 1458, 1437, 1361, 1357, 1320, 1190, 1161 cm$^{-1}$; HRMS (M+H)$^+$ calculated for C$_{15}$H$_{27}$N$_2$O$_6$S 363.1590, found 363.1575.

In this example, methylene chloride was the solvent utilized. However, toluene, benzene, chlorobenzene, dichlorobenzene, DME, and mixtures thereof are also suitable solvents. Furthermore, while Grubbs catalyst 1 was utilized, Grubbs catalyst 2 and/or 3 could be utilized as well. Finally, while the procedure was carried out at temperatures of 4° C., temperatures of anywhere from about 15–80° C. would also be suitable.

Example 4

The inhibition of Herpes Simplex Virus Protease by the compound shown in Scheme R was determined according to the procedure described by Waxman et al., *Antiviral Chemistry and Chemotherapy*, 11:1–22 (1999); Qiu et al., *Proteases of Infectious Agents*, Academic Press, 93–115 (1999); and U.S. Pat. No. 6,008,033, each incorporated by reference herein.

The compound was tested at a concentration of 200 μmolar.

Scheme R

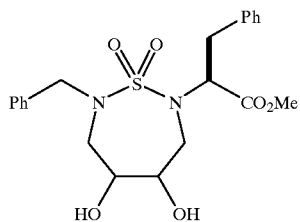

The compound resulted in a 20.5% inhibition of the protease.

Example 5

The inhibition of HIV protease by the compounds shown in Scheme S (99 μmolar), Scheme T (99 μmolar), and Scheme U (99 μmolar) was determined following the procedure described by Maschera et al., Human Immunodeficiency Virus: Mutations in the Viral Protease that Confer Resistance to Saquinavir Increase the Dissociation Rate Constant for the Protease-Saquinavir Complex, *J. Biol. Chem.*, 271:33231–35 (1996), incorporated by reference herein.

Scheme S

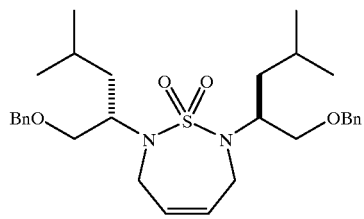

Scheme T

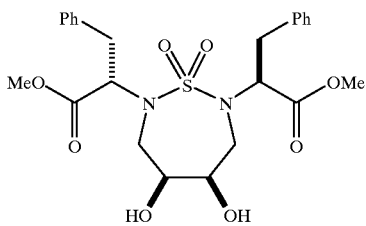

Scheme U

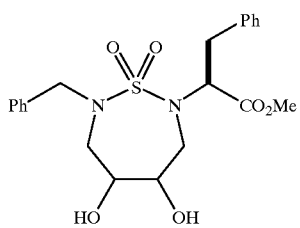

The compound of Scheme S resulted in a 96% inhibition of the protease, while the compound of Scheme T resulted in a 22% inhibition. Finally, the compound of Scheme U resulted in a 21% inhibition.

Example 6

The inhibition of human cathepsin K by the compounds shown in Schemes V (106 μmolar) and W (106 μmolar) was determined.

Scheme V

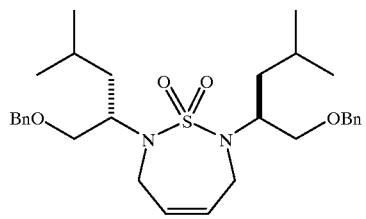

Scheme W

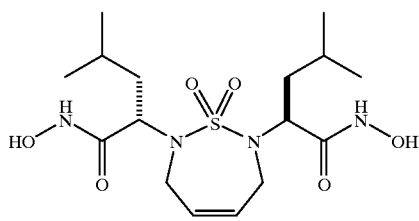

The peptides utilized were chromophoric Z-Phe-Arg-pNA*HCl and fluorogenic Z-Phe-Arg-AMC (each available from BACHEM Bioscience, Inc.). Stock solutions were prepared with 100% dimethylsulfoxide (DMSO) and stored at −20° C.

The final assay conditions were 100 mM NaOAc, pH of 5.5, 10 mM (R,R)-dithiothreitol (DTT), 10% DMSO, 120 mM NaCl, 10 μmolar of the peptide, and 12.5–0.012 μmolar inhibitor in twofold serial dilutions from 20× stocks in 100% DMSO. The enzyme working solution was a 1:3000 dilution of 8.75 mM human cathepsin K into 100 mM of NaOAc, pH of 5.5, 10 mM DTT, 1.2 M NaCl.

Serial dilutions were performed in 100% DMSO. Columns 2–12 of an intermediate plate were filled with 100 mL/well of 100% DMSO and column 1 was filled with 195 mL/well. Next, 5 mL of a 10 mM solution was added to column 1. A twofold serial dilution was prepared in columns 1–11 of the intermediate plate by sequential transfer of 100 mL of the contents of each well in a column to the corresponding well of the next column, with mixing between each transfer. Samples of 11.7 mL from each well of the intermediate plate were transferred to another intermediate plate and 200 mL of a peptide buffer (105 mM NaOAc, pH of 5.5, 10.5 mM DTT, 5.8% DMSO, 12 mM peptide) was added. Samples (20 μL) of enzyme working solution were placed in each well of an empty assay plate, and 180 μL/well of the test compound-peptide mixture was added to the enzyme to initial the assay. The fluorescence was monitored every 6 minutes for 72 minutes using a CytoFluor Series 4000 PerSeptive Biosystems multi-well fluorescence plate reader with the following settings: gain=50; 20 reads/well; 32° C.; lex=360±20 nm; and lem=440±20 nm.

The compound of Scheme V resulted in a 20% inhibition of human cathepsin K, while the compound of Scheme W resulted in a 14% inhibition of human cathepsin K.

We claim:

1. A compound according to a formula selected from the group consisting of

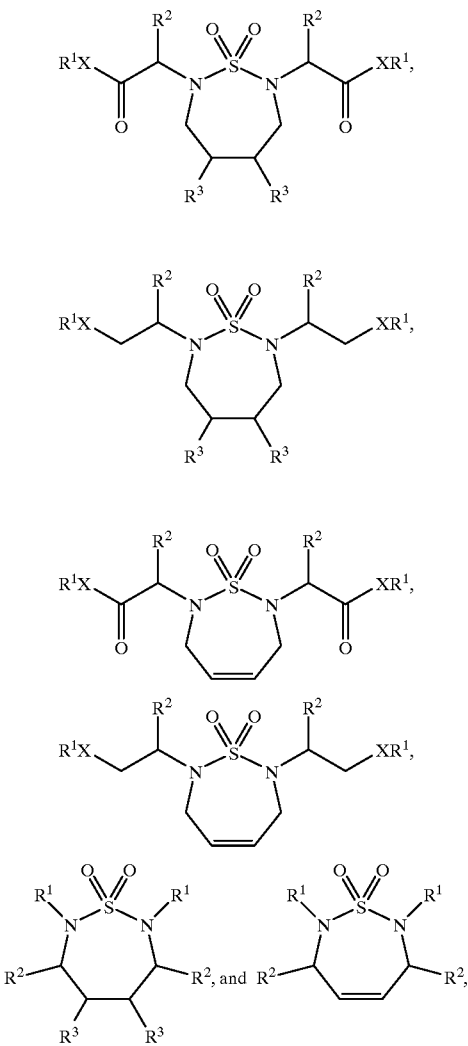

wherein:

each X is individually selected from the group consisting of —O—, —NH—, and —N(OR$^1$)—;

each R$^1$ is individually selected from the group consisting of hydrogen, branched and unbranched alkyl groups, branched and unbranched alkenyl groups, branched and unbranched alkynyl groups, allyl groups, aryl groups, acyl groups, 2–15 mer peptides, and benzyl groups;

each R$^2$ is individually selected from the group consisting of hydrogen, 2–15 mer peptides, and substituted and unsubstituted amino acid side chains selected from the group consisting of

[structures of amino acid side chains shown]

wherein each R$^4$ is individually selected from the group consisting of hydrogen, branched and unbranched alkyl groups, branched and unbranched alkenyl groups, branched and unbranched alkynyl groups, allyl groups, aryl groups, acyl groups, and benzyl groups; and each R$^3$ is individually selected from the group consisting of hydrogen, —OH, and —NHR$^1$.

2. The compound of claim 1, wherein said formula is selected from the group consisting of

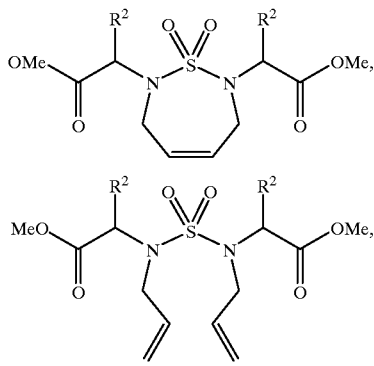

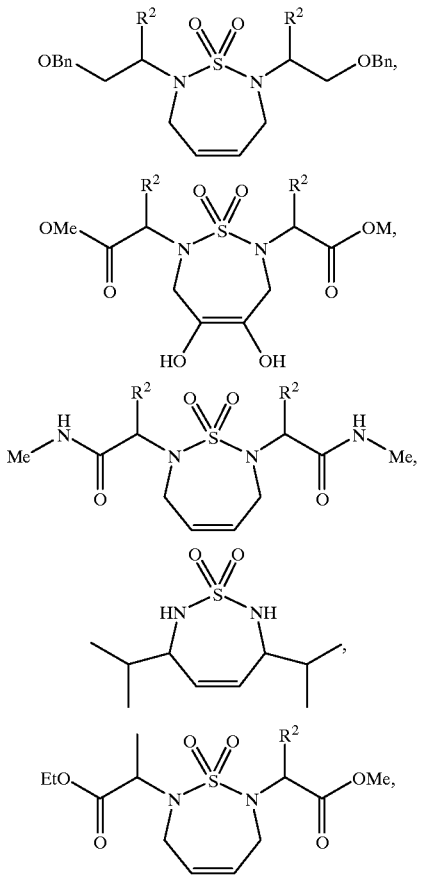

wherein each R² is individually selected from the group consisting of —CH₃, —CH(CH₃)₂, —CH₂CH(CH₃)₂, and —CH₂Ph.

3. A method of forming a sulfamide compound comprising the step of reacting a sulfamide comprising an opened-ring structure with a ring-closing catalyst to yield a 7-membered closed-ring sulfamide compound.

4. The method of claim 3, wherein said ring-closing catalyst is a Grubbs catalyst.

5. The method of claim 4, wherein said Grubbs catalyst is selected from the group consisting of 6. The method of claim 5, wherein said Grubbs catalyst is

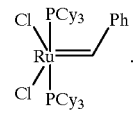

7. The method of claim 3, wherein said opened-ring structure comprises an allylated sulfamide.

8. The method of claim 3, wherein said opened-ring structure is represented by a formula selected from the group consisting of

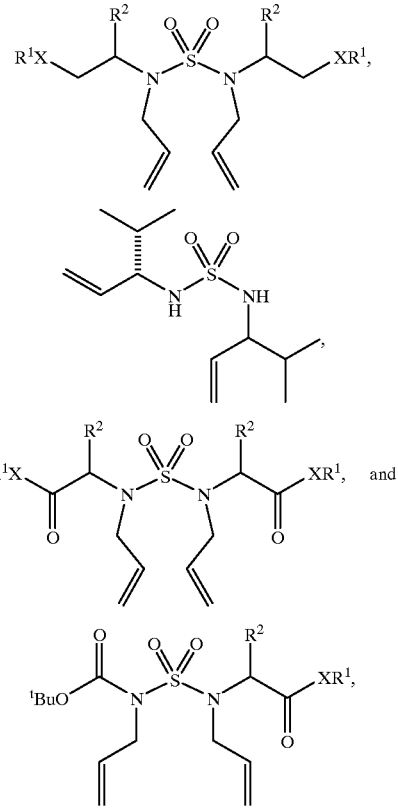

wherein:

each X is individually selected from the group consisting of —O—, —NH—, and —N(OR¹)—;

each R¹ is individually selected from the group consisting of hydrogen, branched and unbranched alkyl groups, branched and unbranched alkenyl groups, branched and unbranched alkynyl groups, allyl groups, aryl groups, acyl groups, 2–15 mer peptides, and benzyl groups; and each R² is individually selected from the group consisting of hydrogen, 2–15 mer peptides, and substituted and unsubstituted amino acid side chains selected from the group consisting of

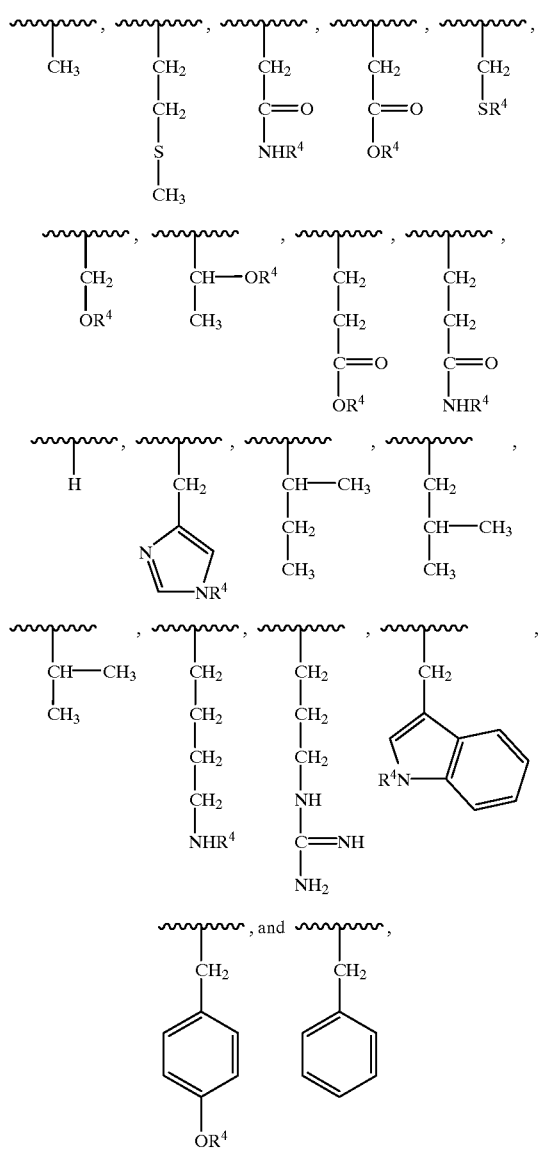

wherein each R[4] is individually selected from the group consisting of hydrogen, branched and unbranched alkyl groups, branched and unbranched alkenyl groups, branched and unbranched alkynyl groups, allyl groups, aryl groups, acyl groups, and benzyl groups.

9. The method of claim 3, wherein said closed-ring structure is represented by a formula selected from the group consisting of

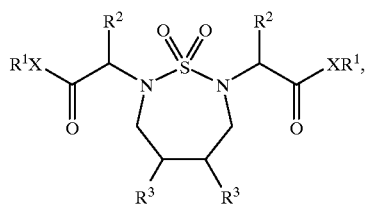

-continued

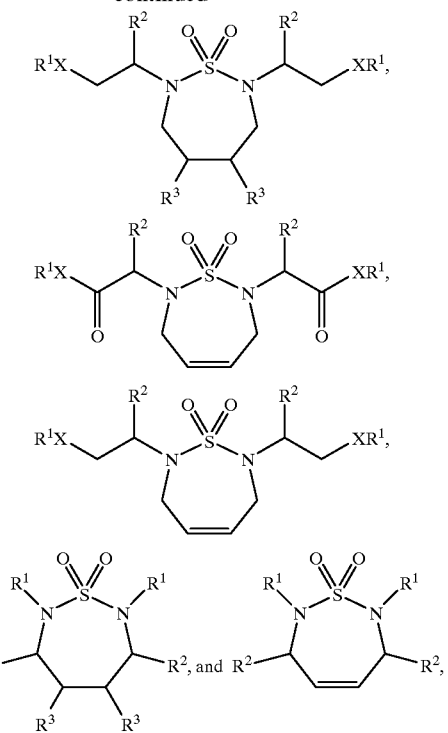

wherein:
each X is individually selected from the group consisting of —O—, —NH—, and —N(OR[1])—;
each R[1] is individually selected from the group consisting of hydrogen, branched and unbranched alkyl groups, branched and unbranched alkenyl groups, branched and unbranched alkynyl groups, allyl groups, aryl groups, acyl groups, 2–15 mer peptides, and benzyl groups;
each R[2] is individually selected from the group consisting of hydrogen, 2–15 mer peptides, and substituted and unsubstituted amino acid side chains selected from the group consisting of

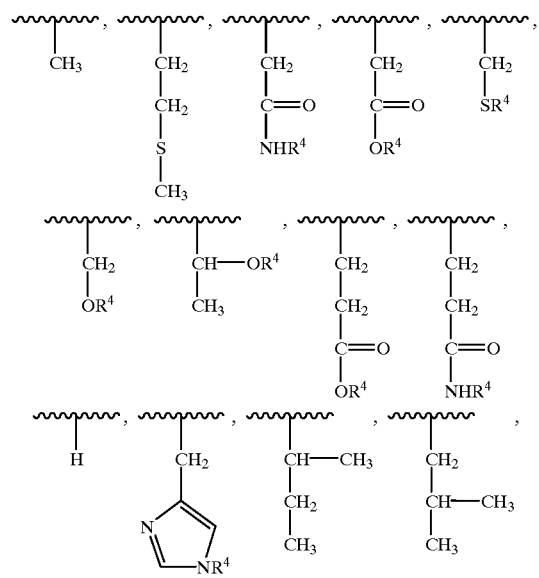

-continued

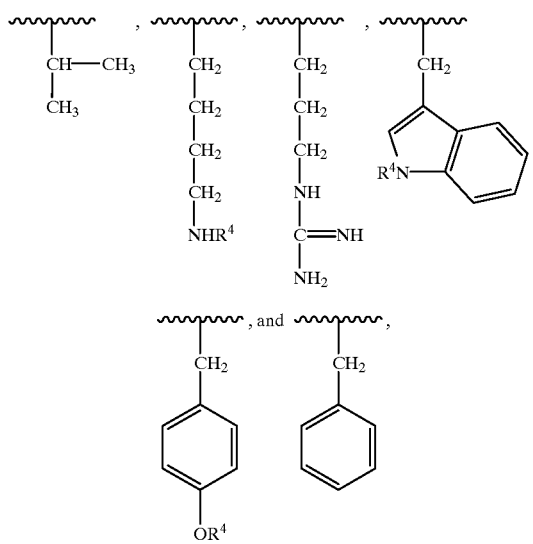

wherein each $R^4$ is individually selected from the group consisting of hydrogen, branched and unbranched alkyl groups, branched and unbranched alkenyl groups, branched and unbranched alkynyl groups, allyl groups, aryl groups, acyl groups, and benzyl groups; and each $R^3$ is individually selected from the group consisting of hydrogen, —OH, and —$NHR^1$.

10. The method of claim 9, wherein said formula is selected from the group consisting of -continued

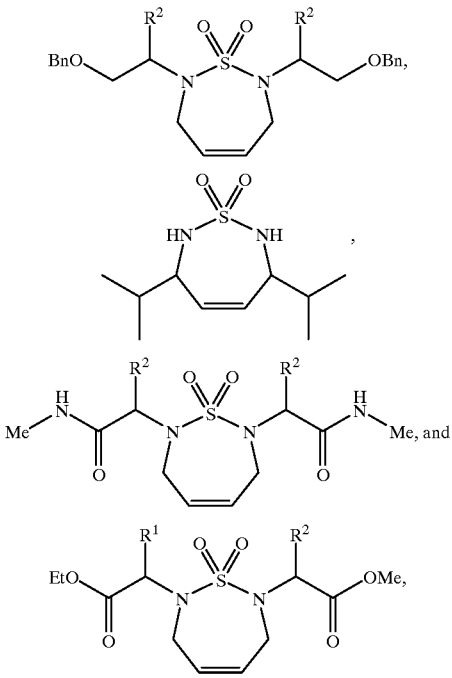

wherein each $R^2$ is individually selected from the group consisting of —$CH_3$, —$CH(CH_3)_2$, —$CH_2CH(CH_3)_2$, and —$CH_2Ph$.

11. The method of claim 3, wherein said reacting step is carried out at a temperature of from about 15–80° C.

12. The method of claim 3, wherein said reacting step is carried out in a solvent system comprising a solvent selected from the group consisting of toluene, benzene, chlorobenzene, dichlorobenzene, methylene chloride, dimethoxyethane, and mixtures thereof.

13. The method of claim 3, wherein said reacting step results in a closed-ring structure yield of at least about 70%.

* * * * *